United States Patent
Miyamoto et al.

(10) Patent No.: US 10,499,629 B2
(45) Date of Patent: Dec. 10, 2019

(54) TRANSPARENT POROUS SUSTAINED-RELEASE BODY AND METHOD FOR PRODUCING THE SAME, AND KIT OF SUSTAINED-RELEASE BODY, SUSTAINED-RELEASE APPARATUS, AND SUSTAINED-RELEASE METHOD

(71) Applicant: SnG INC., Kyoto (JP)

(72) Inventors: Riichi Miyamoto, Kyoto (JP); Hongzhi Bai, Hyogo (JP)

(73) Assignee: SNG INC., Kyoto (JP)

( * ) Notice: Subject to any disclaimer, the term of this patent is extended or adjusted under 35 U.S.C. 154(b) by 0 days.

(21) Appl. No.: 15/748,983

(22) PCT Filed: Aug. 5, 2016

(86) PCT No.: PCT/JP2016/073076
§ 371 (c)(1),
(2) Date: Jan. 30, 2018

(87) PCT Pub. No.: WO2017/026388
PCT Pub. Date: Feb. 16, 2017

(65) Prior Publication Data
US 2019/0008134 A1    Jan. 10, 2019

(30) Foreign Application Priority Data
Aug. 11, 2015  (JP) .................. 2015-158934

(51) Int. Cl.
*A61L 9/00* (2006.01)
*C04B 35/16* (2006.01)
(Continued)

(52) U.S. Cl.
CPC ........ *A01M 1/2027* (2013.01); *A01M 1/2055* (2013.01); *A61L 9/013* (2013.01);
(Continued)

(58) Field of Classification Search
CPC ... A61L 9/00; A61L 9/01; A61L 9/012; A61L 9/013; A01M 1/2027
(Continued)

(56) References Cited

U.S. PATENT DOCUMENTS 4,788,164 A  * 11/1988  Che .................. A01N 25/18
                                                      428/905
5,624,875 A     4/1997  Nakanishi et al.
(Continued)

FOREIGN PATENT DOCUMENTS

JP    H07-41374 A    2/1995
JP    10-71193       3/1998
(Continued)

OTHER PUBLICATIONS

Riichi Miyamoto et al: "Fabrication of large-sized silica monlith exceeding 1000 ml with high structural homogeneity", Journal of separation science., vol. 36, No. 12, Jun. 18, 2013 (Jun. 18, 2013), pp. 1890-1896, (Year: 2013).*
(Continued)

*Primary Examiner* — Monzer R Chorbaji
(74) *Attorney, Agent, or Firm* — Haynes Beffel & Wolfeld LLP

(57) ABSTRACT

The present invention provides a porous sustained-release body in which transparency of a porous carrier changes. The porous sustained-release body includes an inorganic monolithic porous body 1 including a skeleton body 2 of an inorganic compound and air gaps 3,4 having a three-dimensional continuous network structure formed in the skeleton body 2, and a sustained-release liquid absorbed into air gaps 2, 3, wherein the inorganic monolithic porous body 1 is opaque at an initial state, which is a state before absorption of the sustained-release liquid in which air exists in the air gaps, and refractive index of the sustained-release liquid and (Continued)

refractive index of the skeleton body are the same within an error range within which a portion in which the sustained-release liquid is absorbed into the air gaps changes to transparent or semitransparent.

5 Claims, 13 Drawing Sheets

(51) Int. Cl.
| | |
|---|---|
| *C09K 3/00* | (2006.01) |
| *A01M 1/20* | (2006.01) |
| *C01B 33/152* | (2006.01) |
| *C04B 38/00* | (2006.01) |
| *A61L 9/013* | (2006.01) |
| *A61L 9/04* | (2006.01) |
| *A61L 9/12* | (2006.01) |

(52) U.S. Cl.
CPC ............ *A61L 9/046* (2013.01); *C01B 33/152* (2013.01); *C04B 38/00* (2013.01); *C09K 3/00* (2013.01); *A61L 9/12* (2013.01); *A61L 2209/12* (2013.01)

(58) Field of Classification Search
USPC .................. 501/4, 53, 133, 154; 422/5, 120, 422/122–123, 306; 424/76.1, 70.12, 724; 252/385; 106/18.12; 428/404, 36.9
See application file for complete search history.

(56) References Cited

U.S. PATENT DOCUMENTS

| | | | |
|---|---|---|---|
| 6,562,744 | B1 | 5/2003 | Nakanishi et al. |
| 6,565,973 | B2 * | 5/2003 | Duff ..................... B82Y 30/00 |
| | | | 428/402 |
| 2010/0221144 | A1 | 9/2010 | Bedson et al. |
| 2013/0241097 | A1 | 9/2013 | Ippommatsu et al. |
| 2014/0076070 | A1 | 3/2014 | Nakanishi et al. |

FOREIGN PATENT DOCUMENTS

| | | |
|---|---|---|
| JP | H1059742 | 3/1998 |
| JP | H11292528 A | 10/1999 |
| JP | 2000-070352 A | 3/2000 |
| JP | 2000-254217 A | 9/2000 |
| JP | 2002-085543 A | 3/2002 |
| JP | 2005-307120 A | 11/2005 |
| JP | 2007-111281 A | 5/2007 |
| JP | 2012111655 A | 6/2012 |
| JP | 2013-3065 A | 1/2013 |
| JP | 2014-061457 A | 4/2014 |
| JP | 2015-116334 A | 6/2015 |
| WO | 2007021037 A1 | 2/2007 |

OTHER PUBLICATIONS

Miyamoto, et al, "Fabrication of large-sized silica monolith exceeding 1000 mL with high structural homogeneity," Journal of Separation Science, Aug. 2013, vol. 36, Issue. 12, pp. 1890-1896.
Extended European Search Report in 16835085.8 dated Jun. 11, 2018, 12 pages.

* cited by examiner

Initial state (opaque)

Transparent

Semitransparent

Opaque

| Name of slow-release liquid | Refractive index | Through-hole diameter (μm) | | | | | | |
|---|---|---|---|---|---|---|---|---|
| | | 10 | 5 | 2 | 1 | 0.6 | 0.3 | 0.1 |
| Water | 1.333 | × | × | | × | × | × | △ |
| Isopropanol | 1.375 | × | × | | × | × | △ | ○ |
| Dichloromethane | 1.424 | × | × | × | × | △ | ○ | ○ |
| N,N-Dimethylformamide | 1.4305 | △ | △ | △ | △ | △ | | |
| Chloroform | 1.442 | ○ | ○ | ○ | ○ | ○ | | |
| Coconut oil (essential oil) | 1.45 | ○ | ○ | ○ | | | | |
| Lavender (essential oil) | 1.46 | | | ○ | | | | |
| Hinoki (essential oil) | 1.47 | | | ○ | | | | |
| Lemon (essential oil) | 1.472 | | | ○ | | | | |
| Glycerin | 1.473 | ○ | ○ | ○ | ○ | ○ | ○ | ○ |
| Melissa (essential oil) | 1.48 | △ | △ | △ | △ | ○ | | |
| Toluene | 1.49 | | | × | × | ○ | | |
| Ylang-ylang (essential oil) | 1.496 | | | × | × | △ | | |
| Benzene | 1.5012 | × | × | × | × | △ | ○ | ○ |
| Benzonitrile | 1.528 | × | × | × | × | × | ○ | ○ |

Fig. 5

| Name of slow-release liquid | Refractive index | Through-hole diameter | | | | |
|---|---|---|---|---|---|---|
| | | 0.6 μm | 0.3 μm | 0.1 μm | 40nm | 4nm |
| Water | 1.333 | × | × | △ | ○ | △ |
| Isopropanol | 1.375 | × | △ | ○ | ○ | ○ |
| Dichloromethane | 1.424 | ○ | ○ | ○ | ○ | ○ |
| Glycerin | 1.473 | × | ○ | ○ | ○ | ○ |
| Benzene | 1.5012 | × | △ | ○ | ○ | ○ |
| Benzonitrile | 1.528 | | | | | ○ |

Fig. 9

TRANSPARENT POROUS SUSTAINED-RELEASE BODY AND METHOD FOR PRODUCING THE SAME, AND KIT OF SUSTAINED-RELEASE BODY, SUSTAINED-RELEASE APPARATUS, AND SUSTAINED-RELEASE METHOD

TECHNICAL FIELD

The present invention relates to a porous sustained-release body, wherein a sustained-release liquid containing a sustained-release component is absorbed into a porous carrier, and the sustained-release liquid is gradually emanated from the porous carrier by evaporation or volatilization, and specifically relates to a transparent porous sustained-release body wherein a porous carrier is an inorganic monolithic porous body, and the carrier becomes transparent or semitransparent at a state in which a sustained-release liquid is absorbed into the carrier.

BACKGROUND ART

As a porous sustained-release body in which a sustained-release liquid containing a sustained-release component is absorbed into a porous carrier and then emanated gradually, various types of sustained-release components have ever been developed and brought into practical use before (e.g., following Patent Documents 1, 2, and the like). Further, there are sustained-release bodies such as a sustained-release body in which a sustained-release liquid is absorbed into a fibrous carrier (e.g., following Patent Document 1 and the like), a sustained-release body in which a sustained-release liquid is gelled and formed into the sustained-release body without absorption into a porous carrier (e.g., following Patent Document 1, 3, and the like), or a sustained-release body in which a sustained-release liquid is gelled within air gaps of a porous carrier (e.g., following Patent Document 4 and the like).

Further, sustained-release components for general consumers include an aromatic component, a deodorant component, an insecticidal ingredient, and the like. In addition, porous carriers include plant dry matter such as a piece of wood, a potpourri, and the like, an inorganic porous body such as silica gel, zeolite, or unglazed pottery, and the like, an organic porous body such as cellulose beads and the like. In addition, widely used shape of an inorganic porous body and an organic porous body, except for unglazed pottery, is granular shape.

PRIOR ART DOCUMENTS

Patent Documents

Patent Document 1: Japanese Unexamined Patent Publication No. 2000-254217
Patent Document 2: Japanese Unexamined Patent Publication No. 2015-116334
Patent Document 3: Japanese Unexamined Patent Publication No. 2000-70352
Patent Document 4: Japanese Unexamined Patent Publication No. 2007-111281

SUMMARY OF THE INVENTION

Problems to be Solved by the Invention

In the conventional sustained-release body as described above, product development has been made with emphasis on persistence or prompt efficiency of a sustained-release component, and product development with emphasis on reusability of a porous carrier, and functions and design properties except for a sustained-release liquid retentivity of a porous carrier has not been made. Especially, there has never been before, as long as the present inventors know, a porous sustained-release body in which a porous carrier is easily reused as a sustained-release body, initial shape is maintained without changing in shape between before and after use, and transparency of a porous carrier changes such that the porous carrier is opaque at an initial state, which is a state before absorption of a sustained-release liquid, and a portion of the porous carrier into which a sustained-release liquid is absorbed changes to transparent or semitransparent.

In a sustained-release body which is formed by gelation of a sustained-release liquid or a sustained-release body in which a container is filled with a sustained-release liquid, although a transparent or semitransparent sustained-release body exists, since the sustained-release body is not supported by a porous carrier, a volume of the sustained-release body decreases when a sustained-release component is volatilized. Further, also in a sustained-release body, so-called soft gel in which a sustained-release liquid is absorbed into a porous carrier, although a transparent or semitransparent sustained-release body exists, the sustained-release body swells when a sustained-release liquid is absorbed, and shrinks when the sustained-release liquid is volatilized, and thus the sustained-release body changes in a volume and shape. Both of the above-described transparent or semitransparent sustained-release bodies can be used only once.

Most of the porous sustained-release bodies are opaque. This is because the porous carrier itself is an opaque material, or because, even if the porous carrier itself is a transparent material, there is a large difference in refractive index between the porous carrier and a sustained-release liquid absorbed into pores which exists irregularly in the porous carrier, and thus a light is irregularly reflected and transmitted at an interface between a sustained-release liquid in the pores and the porous carrier, which leads to opaque appearance when the porous carrier is observed from the outside.

Since a granular silica gel has a porous carrier with a refractive index of about 1.5 and is transparent, and some oil containing an aromatic component such as an essential oil has refractive index of around 1.5, when the granular silica gel is used in combination with such an essential oil and the like, the granular silica gel can be transparent or semitransparent. There are silica gels having particle diameters of from several micrometers to several millimeters. When the particle diameter is large, a porosity of the silica gel is as small as from 10 to 20% and a surface area of the silica gel as a particle is large, and thus volatilization or evaporation of a sustained-release liquid such as an essential oil is accelerated, and persistence, which is a sustained-release efficacy, is poor. On the other hand, when a particle diameter is small, the porosity can be improved to as large as about 40 to 50%, however, when a particle diameter is minute, for example, 200 μm or less, the silica gel can easily be dispersed into the air, and thus handling of the silica gel is very difficult, which leads to a problem regarding reusability. In addition, since such a silica gel is granular, an additional container for including the silica gel is required. Further, a granulated and compression molded silica gel has a low porosity, and thus an amount of a sustained-release liquid such as an essential oil absorbed and an absorption rate is small, which leads to a problem when the silica gel is reused.

Further, in order to maintain whole of the granular silica gel, which is included in a transparent container and the like, transparent or semitransparent, voids between particles of silica gel is also required to be filled with a sustained-release liquid such as an essential oil and the like, and then there is a risk that the sustained-release liquid between the particles is volatilized or evaporated earlier than the sustained-release liquid absorbed into the particles. As a result, even if each of the particles are transparent or semitransparent, when air exists between the minute particles and whole of the granular silica gel is observed from the outside, although a large amount of the sustained-release liquid remains in the particles, the silica gel sometimes can be opaque because a light is irregularly reflected and transmitted at an interface between the particles and the air.

On the other hand, there is other porous carrier having a high porosity in addition to a silica gel having a small particle diameter, however, such a porous carrier has low affinity for, for example, an essential oil, and has a low rate of absorption of the sustained-release liquid into the porous carrier, and most of the above-described porous carriers are hard to used when the porous carriers are reused.

An object of the present invention is to provide a porous sustained-release body having properties that are hard to be achieved by the above-described conventional sustained-release body in which a porous carrier is easily reused as a sustained-release body, initial shape is maintained without changing in shape between before and after use, and transparency of the porous carrier changes such that the porous carrier is opaque at an initial state, which is a state before absorption of a sustained-release liquid, and a portion of the porous carrier into which a sustained-release liquid is absorbed changes to transparent or semitransparent, wherein a high persistence is maintained, at the same time functions and design properties other than the above-described persistence can be pursued.

Means for Solving the Problem

A first aspect of the present invention provides, for achieving the above-mentioned objects, a transparent porous sustained-release body which includes an inorganic monolithic porous body having a skeleton body of an inorganic compound and having air gaps having a three-dimensional continuous network structure, and a sustained-release liquid absorbed into said air gaps, wherein said inorganic monolithic porous body is opaque at an initial state, which is a state before absorption of said sustained-release liquid in which air exists in said air gaps, and a refractive index of said sustained-release liquid and a refractive index of said skeleton body are the same within an error range within which a portion in which said sustained-release liquid is absorbed into said air gaps changes to transparent or semitransparent.

Then, in the present invention, "transparent" refers to a condition in which, for example, a character or a figure behind an inorganic monolithic porous body can be recognized through the inorganic monolithic porous body. Further, "semitransparent" refers to a condition in which, although transparency is reduced as compared to "transparent" by cloudiness or the like, for example, a character or a figure behind an inorganic monolithic porous body can be recognized through the inorganic monolithic porous body. "Opaque" refers to a condition in which, for example, a character or a figure behind an inorganic monolithic porous body cannot be recognized through the inorganic monolithic porous body.

Further, in the present invention, a monolithic porous body is not a granular or powdered porous body in which a lot of the porous bodies are included in a container for use, but is a mass of porous body having any shape and can be used individually.

Further, for achieving the above-mentioned object, a first aspect of the present invention provides a sustained-release method which comprises: using an inorganic monolithic porous body including a skeleton body of an inorganic compound and air gaps having a three-dimensional continuous network structure in which the inorganic monolithic porous body is opaque at an initial state in which air exists in said air gaps; infiltrating a sustained-release liquid, in which a refractive index of the sustained-release liquid and a refractive index of said skeleton body are the same within an error range within which a portion into which said sustained-release liquid is absorbed into said air gaps changes to transparent or semitransparent, into said air gaps to change said inorganic monolithic porous body from an opaque state, which is said initial state, to a transparent or semitransparent state at a portion in which said sustained-release liquid is absorbed into said air gaps; and then carrying out gradual emanation of said sustained-release liquid from said inorganic monolithic porous body to recover an opaque state at a portion at which said sustained-release liquid is emanated from said air gaps.

Further, in the transparent porous sustained-release body and the sustained-release method according to the above-mentioned first aspect, a second aspect of the present invention is characterized in that said skeleton body has a three-dimensional continuous network structure, said air gaps have a two-step hierarchical porous structure including through-holes and pores, the through-holes being formed in voids in said skeleton body and having a three-dimensional continuous network structure, and the pores extending from a surface to an inside of said skeleton body and being dispersively formed on said surface, a most frequent pore diameter in a pore diameter distribution of said pores is within a range of 2 nm or more and 200 nm or less, and a most frequent pore diameter in a pore diameter distribution of said through-holes is equal to or more than 5 times of said most frequent pore diameter of the pores, and within a range of 0.1 μm or more and 100 μm or less.

Further, in the transparent porous sustained-release body and the sustained-release method according to the above-mentioned aspects, a third aspect is characterized in that said skeleton body has a three-dimensional continuous network structure, said air gaps have a one-step porous structure including through-holes formed in voids in said skeleton body and having a three-dimensional continuous network structure, and a most frequent pore diameter in a pore diameter distribution of said through-holes is within a range of 2 nm or more and 100 μm or less.

Further, it is preferable that in the transparent porous sustained-release body and the sustained-release method of the above-mentioned second aspect, a most frequent pore diameter in a pore diameter distribution of said through-holes is 0.6 μm or less.

Further, it is preferable that in transparent porous sustained-release body and the sustained-release method according to the above-mentioned second or third aspect, a most frequent pore diameter in a pore diameter distribution of said through-holes is 0.3 μm or less.

Further, it is preferable that in the transparent porous sustained-release body and the sustained-release method according to any of the above-mentioned aspects, said inorganic compound is a silicon oxide composite mainly containing silica or silicon oxide.

Further, it is preferable that in the transparent porous sustained-release body and the sustained-release method according to any of the above-mentioned aspects, said sustained-release liquid is an essential oil having a refractive index within a range of 1.4 to 1.6, and the refractive index of the essential oil is the same relative to the refractive index of said skeleton body within said error range.

Further, for achieving the above-mentioned object, one aspect of the present invention provides a kit of sustained-release body in which said inorganic monolithic porous body and said sustained-release liquid constituting the transparent porous sustained-release body according to any of the above-mentioned aspects are separately included in a state in which said sustained-release liquid is not absorbed into said air gaps of said inorganic monolithic porous body.

Further, one aspect of the present invention preferably provides a sustained-release apparatus including the transparent porous sustained-release body according to any of the above-mentioned aspects or the kit of sustained-release body according to the above-mentioned aspect, and a light source, which irradiates said inorganic monolithic porous body with light.

Further, it is preferable that in the sustained-release method according to any of the above-mentioned aspects, said inorganic monolithic porous body is irradiated with light during a process in which said sustained-release liquid is emanated from said inorganic monolithic porous body.

Further, for achieving the above-mentioned object, one aspect of the present invention provides a method for producing a transparent porous sustained-release body which comprises a step of providing separately said inorganic monolithic porous body and said sustained-release liquid constituting the transparent porous sustained-release body according to any of the above-mentioned aspects, and a step of infiltrating said sustained-release liquid into said air gaps to change said inorganic monolithic porous body from an opaque state, which is said initial state, to a transparent or semitransparent state at a portion in which said sustained-release liquid is absorbed into said air gaps.

Effects of the Invention

According to the transparent porous sustained-release body and the sustained-release method according to any of the above-mentioned aspects, it is possible to achieve a porous sustained-release body and a sustained-release method in which an inorganic monolithic porous body, which is a porous carrier, is easily reused as a sustained-release body, an initial shape is maintained without changing in shape between before and after use, and transparency of a porous carrier changes such that the porous carrier is opaque at an initial state, which is a state before absorption of a sustained-release liquid, and a portion into which a sustained-release liquid is absorbed changes to transparent or semitransparent, wherein a high persistence is maintained, at the same time a visual effect or an optical effect associated with the change in transparency is included as an added value, and the design is excellent.

Further, according to the kit of sustained-release body and the method for producing the transparent porous sustained-release body according to the above-mentioned aspect, a transparent porous sustained-release body having the above-mentioned excellent properties can easily be prepared.

Further, according to the sustained-release apparatus according to the above-mentioned aspect, using transparency of the inorganic monolithic porous body, an application in which a visual effect or an optical effect owing to a light emitted from a light source is enjoyed is added. Further, change in a visual effect or an optical effect owing to change of the inorganic monolithic porous body in transparency associated with evaporation or volatilization of a sustained-release liquid can also be enjoyed.

BRIEF DESCRIPTION OF THE DRAWINGS

FIG. 5 is a list table showing results of evaluation of transparency with respect to silica monoliths according to the first embodiment.

FIG. 9 is a list table showing results of evaluation of transparency with respect to silica monoliths according to the second embodiment.

FIG. 11 is a view schematically showing one example of application an inorganic monolithic porous body to a brooch or the like.

DESCRIPTION OF EMBODIMENTS

Embodiments of a transparent porous sustained-release body, a kit of sustained-release body, a sustained-release method, a sustained-release apparatus, and a method for producing a transparent porous sustained-release body according to the present invention will be described with reference to drawings.

First Embodiment

First, a structural feature of a transparent porous sustained-release body according to one embodiment will be described. A transparent porous sustained-release body is constituted by absorption of a sustained-release liquid into air gaps of an inorganic monolithic porous body 1.

Figure 1:
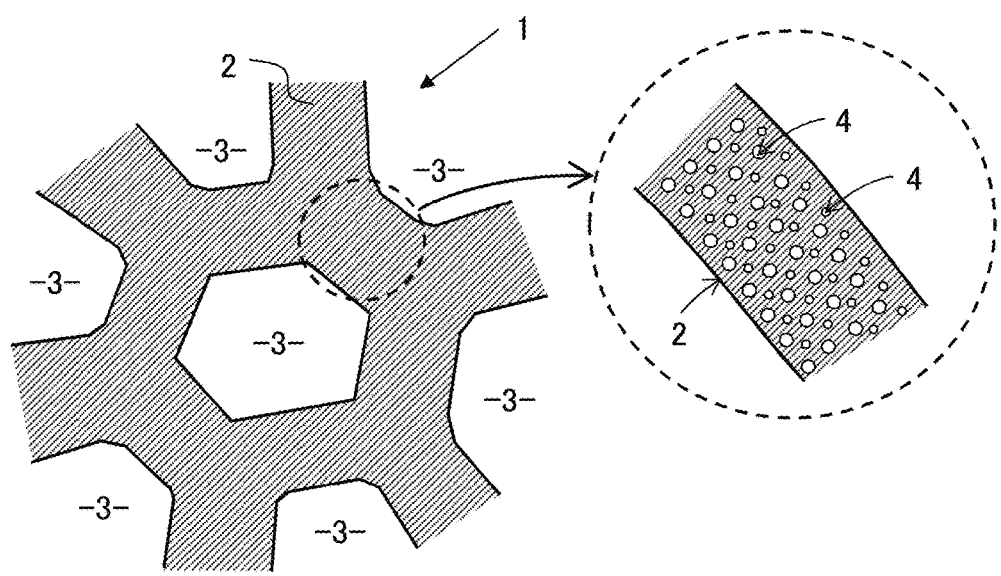
FIG. 1 is a sectional view schematically and two-dimensionally showing a structural feature of an inorganic monolithic porous body according to the first embodiment.

In this embodiment, as schematically and two-dimensionally shown in FIG. 1, an inorganic monolithic porous body 1 includes a skeleton body 2 including an inorganic compound having a three-dimensional continuous network structure, and has a two-step hierarchical porous structure including through-holes 3 formed in voids in the skeleton body 2, and pores 4 extending from a surface to the inside of the skeleton body 2 and dispersively formed on the surface. Air gaps of the inorganic monolithic porous body 1 include the through-holes 3 and pores 4. In this specification, the "surface of the skeleton body" refers to a surface of the skeleton body exposed toward the through-hole, and does not include the inner wall surface of the pore formed in the skeleton body. When the inner wall surface of the pore is included, the surface is referred to as a "total surface of the skeleton body". Further, a surface exposed toward the outside of the inorganic monolithic porous body 1 is simply referred to as an "exposed surface". The through-hole and the pore may also be referred to as a macropore and a mesopore, respectively.

In this embodiment, the inorganic compound that forms the skeleton body 2 is assumed to be silica gel or silica glass ($SiO_2$). In an inorganic monolithic porous body 1 (hereinafter, referred to as a "silica monolith" as necessary), the most frequent pore diameter $\phi 0$ m in the pore diameter distribution of pores 4 is within a range of 2 nm or more and 200 nm or less, and the most frequent pore diameter $\phi 1$ m in the pore diameter distribution of through-holes 3 is equal to or more than 5 times of the most frequent pore diameter $\phi 0$ m of pores 4, and within a range of 0.1 μm or more and 100 μm or less. Then, each of the above-described ranges of the most frequent pore diameter $\phi 1$ m of the through-holes 3 and the most frequent pore diameter $\phi 0$ m of the pores 4 is a range which can be obtained by synthesis of an inorganic monolithic porous body 1 having a two-step hierarchical porous structure by a spinodal decomposition sol-gel method as described below. That is, it means that the most frequent pore diameter $\phi 0$ m and the most frequent pore diameter $\phi 1$ m are not limited to a specific value. However, when the most frequent pore diameter $\phi 1$ m of through-holes 3 is limited to 0.6 μm or less, more preferably 0.3 μm or less, freedom in selection of a sustained-release liquid used can be extended. Then, the limitation that the most frequent pore diameter $\phi 1$ m is equal to or more than 5 times of the most frequent pore diameter $\phi 0$ m has been created from experience because there is a difference between the through-holes 3 which is formed in voids in the skeleton body 2 and the pores 4 which extends from a surface to an inside of the skeleton body 2, and because a pore diameter of the through-holes 3 is equal to or larger than a diameter of the skeleton body 2.

Figure 2:
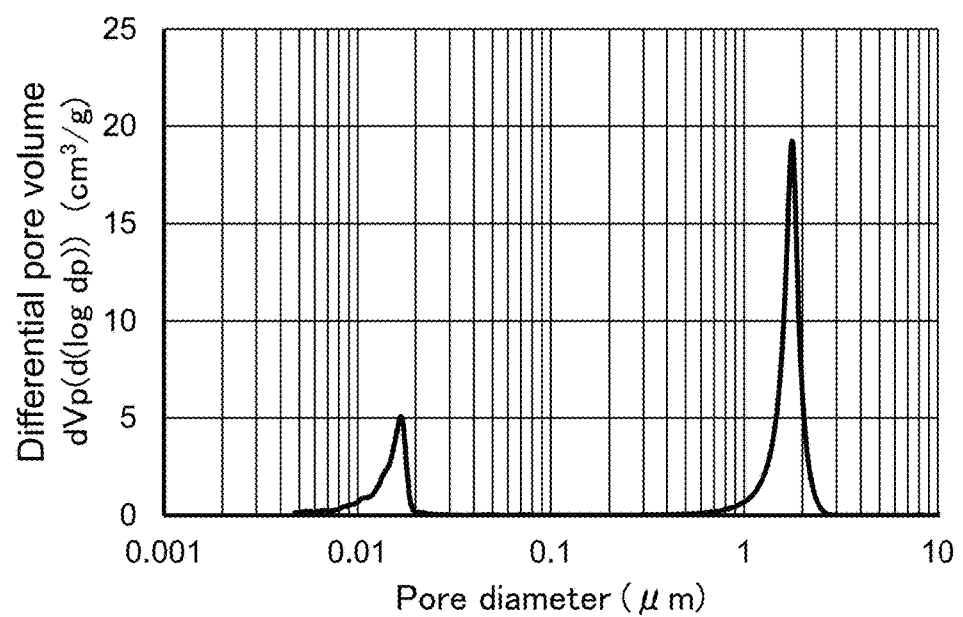
FIG. 2 is a view showing an example of a pore diameter distribution of through-holes and pores of a silica monolith according to the first embodiment.

Each of the most frequent pore diameters of through-holes 3 and pores 4 is a most frequent value (mode value) in a pore diameter distribution as measured by a well-known mercury press-in method. As the pore diameter distribution of pores 4, one derived by a well-known BJH method based on nitrogen adsorption measurement may be used. In addition, the most frequent pore diameter $\phi 1$ m of through-holes 3 is not much different from an average pore diameter derived as an average of through-hole diameters measured at 20 to 30 arbitrary dispersed points in an electron micrograph of the skeleton body 2. FIG. 2 shows an example of pore diameter distributions of through-holes 3 and pores 4 as measured by a mercury press-in method. The abscissa represents the pore diameters (unit: μm) of through-holes 3 and pores 4, and the ordinate represents a differential pore volume (unit: $cm^3/g$). However, the differential pore volume also includes the differential through-hole volume. The peak on the left side shows the most frequent pore diameter $\phi 0$ m of pores 4, and the peak on the right side shows the most frequent pore diameter $\phi 1$ m of through-holes 3. In the example in FIG. 2, the most frequent pore diameters of through-holes 3 and pores 4 are about 1.77 μm and about 17 nm, respectively, the half-widths of through-holes 3 and pores 4 are about 0.34 μm and about 3.4 nm, respectively. Hereinafter, unless otherwise specified, a most frequent pore diameter in a pore diameter distribution of through-holes 3 is sometimes simply referred to as "through-hole diameter", and a most frequent pore diameter in a pore diameter distribution of pores 4 is sometimes simply referred to as "pore diameter".

Figure 3:
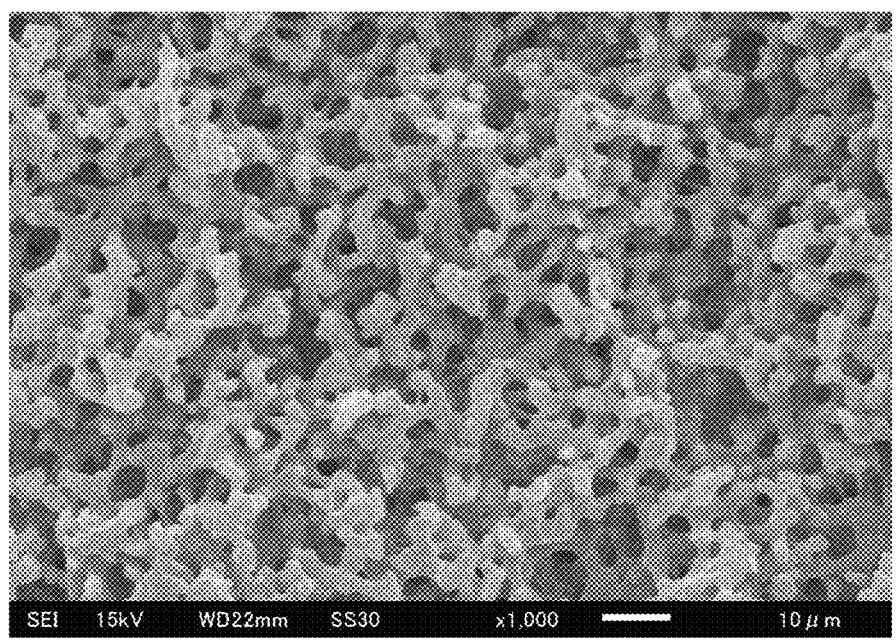
FIG. 3 is a SEM photograph showing an example of a three-dimensional continuous network structure of the silica monolith according to the first embodiment.
Figure 4A:
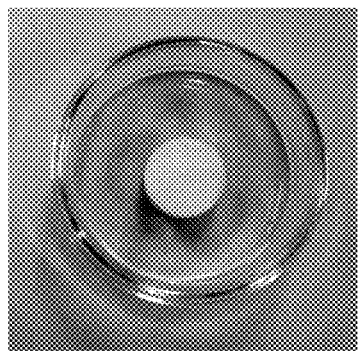
FIGS. 4(A) to 4(D) are photographs demonstrating changes in transparency of the silica monolith (initial state, transparent, semitransparent, and opaque) according to the first embodiment.
Figure 4B:
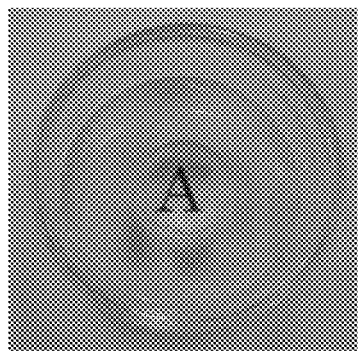
Figure 4C:
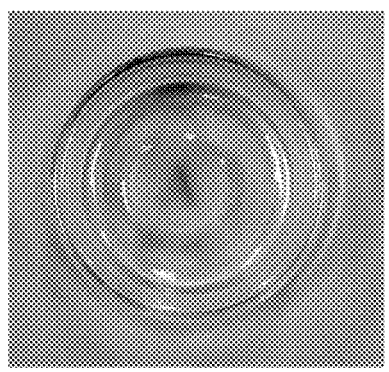
Figure 4D:
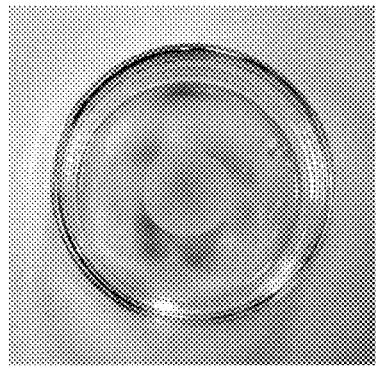

In the present embodiment, a silica monolith is synthesized by a spinodal decomposition sol-gel method as described in detail below. FIG. 3 shows an example of a SEM (scanning electron microscope) photograph showing a three-dimensional continuous network structure of the silica monolith. Next, a method for preparing an inorganic monolithic porous body 1 will be described. The preparation method is divided into a sol preparation step, a gelation step, and a removal step.

In the sol preparation step, a silica precursor as a raw material of silica gel or silica glass, and a coexisting substance serving to induce sol-gel transition and phase separation in parallel are added in an acid or alkaline aqueous solution, and at a low temperature of, for example, 5° C. or lower at which sol-gel transition hardly proceeds, the mixture is stirred to cause a hydrolysis reaction, so that a uniform precursor sol is prepared.

As a main component of the silica precursor, water glass (sodium silicate aqueous solution), or an inorganic or organic silane compound can be used. Examples of the inorganic silane compound include tetraalkoxysilanes such as tetramethoxysilane, tetraethoxysilane, tetra-isopropoxysilane, tetra-n-butoxysilane and tetra-t-butoxysilane. Examples of the organic silane compound include trialkoxysilanes such as trimethoxysilane, triethoxysilane, triisopropoxysilane and trip henoxysilane, dialkoxysilanes such as methyldiethoxysilane, methyldimethoxysilane, ethyldiethoxysilane and ethyldimethoxysilane, monoalkoxysilanes such as dimethylethoxysilane and dimethylmethoxysilane, and the like, each of which has a substituent such as methyl, ethyl, propyl, butyl, hexyl, octyl, decyl, hexadecyl, octadecyl, dodecyl, phenyl, vinyl, hydroxyl, ether, epoxy, aldehyde, carboxyl, ester, thionyl, thio and amino. Alkoxysilicates containing a crosslinking reaction rate controlling group substituent such as a monoalkyl, a dialkyl and a phenyltriethoxy, oligomers such as a disilane being a dimer of the alkoxysilicate and a trisilane being a trimer of the alkoxysilicate, and the like are also considered as the silica precursors. Various compounds are commercially available as the hydrolyzable silane described above, and can be readily and inexpensively acquired, and it is easy to control a sol-gel reaction for forming a three-dimensional crosslinked body including a silicon-oxygen bond.

The acid or alkaline aqueous solution is an aqueous solution in which an acid or a base functioning as a catalyst for promoting a hydrolysis reaction of a silica precursor is dissolved in water as a solvent. Specific examples of the acid include acetic acid, hydrochloric acid, sulfuric acid, nitric acid, formic acid, oxalic acid and citric acid, and specific examples of the base include sodium hydroxide, potassium hydroxide, aqueous ammonia, sodium carbonate, sodium hydrogen carbonate, amines such as trimethyl ammonium, ammonium hydroxides such as tert-butyl ammonium hydroxide, and alkali metal alkoxides such as sodium methoxide. Specific examples of the coexisting substance include polyethylene oxide, polypropylene oxide, polyacrylic acid, block copolymers such as polyethylene oxide-polypropylene oxide block copolymers, cationic surfactants such as cetyltrimethylammonium chloride, anionic surfactants such as sodium dodecyl sulfate, and nonionic surfactants such as polyoxyethylene alkyl ethers. Water is used as a solvent, but an alcohol such as methanol or ethanol may be used.

In the gelation step, the precursor sol prepared in the sol preparation step is injected into a gelation container, and gelled at a temperature of, for example, about 40° C. at which sol-gel transition easily proceeds. Here, in the precursor sol, a coexisting substance serving to induce sol-gel transition and phase separation in parallel is added, and therefore spinodal decomposition is induced to gradually form a co-continuous structure of a silica hydrogel (wet gel) phase and a solvent phase which has a three-dimensional continuous network structure.

In the gelation step, a polycondensation reaction of the wet gel slowly progresses to cause shrinkage of the gel even after the silica hydrogel phase is formed, and therefore, as a step subsequent to the gelation step, the co-continuous structure of the silica hydrogel phase and the solvent phase which is formed in the gelation step is immersed in a basic aqueous solution such as aqueous ammonia, and subjected to a heating treatment in a pressurized container to further promote the hydrolysis reaction, the polycondensation reaction and a dissolution and reprecipitation reaction of the silica hydrogel phase, so that the skeleton structure of the silica hydrogel phase can be further strengthened. The step subsequent to the gelation step may be carried out as necessary. The heating treatment is not necessarily required to be performed in a pressurized container or a closed container, but since an ammonia component or the like may be generated or volatilized by heating, it is preferable to perform the heating treatment in a closed container or a container having pressure resistance.

As the dissolution and rep recipitation reaction of silica fine particles forming the skeleton body of the silica hydrogel phase proceeds, the diameter of pore formed in the skeleton body is increased. Further, when the dissolution and reprecipitation reaction is repeated in hydrothermal treatment, it is possible to perform control to further increase the pore diameter. The control of the pore diameter can also be performed by adding urea in the precursor sol besides a catalyst and a coexisting substance. Urea is hydrolyzed at a temperature of 60° C. or higher to produce ammonia, and the pore diameter of the pore formed in the skeleton body of the wet gel synthesized in the gelation step is increased by the ammonia. Thus, it is possible to control the pore diameter by adding urea. On the other hand, control of the structure and pore diameter of the through-hole is made possible by adjusting the amount of water or the silica precursor added to the precursor sol in the sol preparation step, or the composition and addition amount of the coexisting substance.

Subsequently, in the removal step, washing and drying, or only drying of the wet gel is performed to remove the solvent phase containing additives, unreacted substances and the like. The space after removal of the solvent phase forms a through-hole. By washing, a surface tension during drying which is caused by additives, unreacted substances and the like remaining in the solvent phase can be eliminated to suppress distortion and cracking in the gel during drying. A washing liquid is desirably a liquid such as an organic solvent or an aqueous solution. A liquid in which an organic compound or an inorganic compound is dissolved can also be used. Further, even if a solution having a pH different from the isoelectric point of the gel, such as an acid or an alkali, is used as the washing liquid, additives and the like remaining in the gel can be easily removed. Specifically, various kinds of acids such as hydrochloric acid, sulfuric acid, nitric acid, hydrofluoric acid, acetic acid, formic acid, carbonic acid, citric acid and phosphoric acid, and various kinds of bases such as sodium hydroxide, potassium hydroxide, ammonia, water-soluble amine, sodium carbonate and sodium hydrogen carbonate can be used. For drying the wet gel, natural drying may be adopted, and for eliminating distortion and cracks generated in drying of the wet gel, it is also preferable to adopt drying that is performed after replacement of a solvent in the wet gel by a solvent having a low surface tension lower than that of water, such as isopropanol, acetone, hexane and hydrofluorocarbon; drying by freezing and sublimation; supercritical drying that is performed in a non-surface-tension state after exchange of a solvent in the wet gel with supercritical carbon dioxide; or the like.

Subsequently, the resulting dried gel can be sintered by firing to obtain silica glass. When the firing temperature is lower than the glass transition temperature (about 1000° C.) of silica, silica glass is not formed.

By passing through the above sol preparation step, gelation step and removal step, an inorganic monolithic porous body 1 of dried silica gel or silica glass of three-dimensional continuous network structure which has a two-step hierarchical porous structure is obtained.

In the silica monolith prepared by the above-described manner, at an initial state after preparation, there is not a sustained-release liquid, but air having a refractive index of 1.000293 exists in the air gaps (through-holes 3 and pores 4). On the other hand, since a skeleton body 2 is silica gel or silica glass which have a refractive index of about 1.45 to 1.5, there is a difference in refractive index of about 0.45 to 0.5 at the total surface of the skeleton body 2. Further, since the through-holes 3 is formed, in a similar manner to the skeleton body 2, in voids of the skeleton body 2 in a form of the three-dimensional continuous structure network, and an infinite number of pores are formed on the surface of the skeleton body 2, an incident light from the outside into the silica monolith repeats multiplex irregular reflection and refraction at an interface between a skeleton body 2 and the air in the air gaps due to the above-described difference in refractive index, and thus the initial state silica monolith appears to be cloudy and opaque from the outside. Further, porosity of the silica monolith prepared by the above-described manner can be 50% or more, and a silica monolith in Examples as described below has a high porosity of 85% to 90%.

A sustained-release liquid to be absorbed into air gaps of a silica monolith is not limited to a specific liquid as long as the silica monolith is changed from an opaque state to a transparent or semitransparent state after the sustained-release liquid is absorbed into the silica monolith. That is, any liquid can be accepted as long as a refractive index of a sustained-release liquid and a refractive index of the skeleton body 2 are the same within an error range within which a portion in which the sustained-release liquid is absorbed into air gaps becomes transparent or semitransparent. However, a silica monolith is preferably transparent rather than semitransparent after absorption of a sustained-release liquid because a visual effect and an optical effect are more remarkable, and thus a sustained-release liquid is preferably a liquid with which a silica monolith is changed to a transparent state.

The reason for transparency or semitransparency of a portion in which a sustained-release liquid is absorbed into air gaps is that a difference in refractive index at an interface between a skeleton body 2 and a sustained-release liquid in the air gaps is smaller than the difference in refractive index at the above-described initial state, and thus an extent of reflection and refraction due to the difference in refractive index at the interface is reduced from that at the above-described initial state. However, when a difference in refractive index between the sustained-release liquid and the skeleton body 2 is not sufficiently small, that is, the difference is not within the above-described error range, the extent of reflection and refraction at the interface is not sufficiently reduced, and thus the portion becomes cloudy and opaque.

As a sustained-release liquid, any liquid can be selected as necessary according to an expected effect due to sustained-release of the sustained-release liquid under the above-described refractive index conditions. For example, when a transparent porous sustained-release body is used as an aromatic material, as a sustained-release liquid, an aromatic oil (an essential oil) having a refractive index which is the same as a refractive index of the skeleton body 2 within the above-described error range can be used. There are a lot of aromatic oils having a refractive index of within a range of 1.4 to 1.6, which is close to a refractive index of about 1.45 to 1.5 for silica, and thus a lot of aromatic oils have a refractive index which is the same as that of silica within the above-described error range, and thus various aromatic oils can be selected. In the description below, an error range within which a portion in which a sustained-release liquid is absorbed into air gaps becomes transparent or semitransparent is defined as a "first error range", and an error range within which a portion in which a sustained-release liquid is absorbed into air gaps becomes transparent is defined as a "second error range", for the sake of convenience. Needless to say, the "second error range" is narrower than the "first error range". Further, a difference in refractive index is represented by a difference (a positive value) obtained by subtraction of a smaller refractive index from a larger refractive index. Then, the above-described first and second error range are not, as described below, fixed range, but they vary according to the distribution range of through-holes 3, and also slightly vary with presence or absence of pores.

FIG. 4 provides photographs showing flat and cylindrical silica monoliths (diameter: 10 mm, thickness: 5 mm) having 4 types of states (in total) including an initial state, and transparent, semitransparent, and opaque states in which 3 types of liquids having different refractive indexes are respectively absorbed into the silica monoliths. FIG. 4(A) shows an appearance of a silica monolith at the initial state placed on a transparent glass laboratory dish, and the appearance is completely cloudy and opaque. FIG. 4(B) shows an appearance of a silica monolith placed on a transparent glass laboratory dish changed to transparent by absorption of aromatic oil, and a character "A" in the background beneath the glass laboratory dish can be clearly recognized through the silica monolith and the glass laboratory dish. FIG. 4(C) shows an appearance of a silica monolith placed on a transparent glass laboratory dish changed to semitransparent by absorption of other aromatic oil, and the silica monolith is slightly cloudy, however, a character "A" in the background beneath the glass laboratory dish can be recognized through the silica monolith and the glass laboratory dish. FIG. 4(D) shows that an appearance of a silica monolith is also opaque when the silica monolith is placed on a glass laboratory dish and a yet other aromatic oil is absorbed, and the silica monolith is cloudier than the semitransparent state of FIG. 4(C), and a character "A" in the background beneath the glass laboratory dish cannot be recognized through the silica monolith and the glass laboratory dish. However, it is understood that an extent of cloudiness in the opaque state of FIG. 4(D) is smaller than that in the opaque state at the initial state of FIG. 4(A). The extents of cloudiness between FIG. 4(A) and FIG. 4(D) are different because although both of a difference in refractive index between a skeleton body and air, and a difference in refractive index between a skeleton body and aromatic oil at the initial state are larger than the above-described first error range, the latter difference in refractive index is smaller than the former difference in refractive index.

Then, by using a combination of silica monoliths with different through-hole diameters having a two-step hierarchical porous structure synthesized by a spinodal decomposition sol-gel method as described above and various sustained-release liquids having different refractive indexes, a result of investigating an allowable range of a difference in refractive index between a refractive index of a skeleton body in which a portion in which a sustained-release liquid is absorbed into air gaps becomes transparent or semitransparent, and a refractive index of the sustained-release liquid (the above-described error range) will be described.

Figure 6:
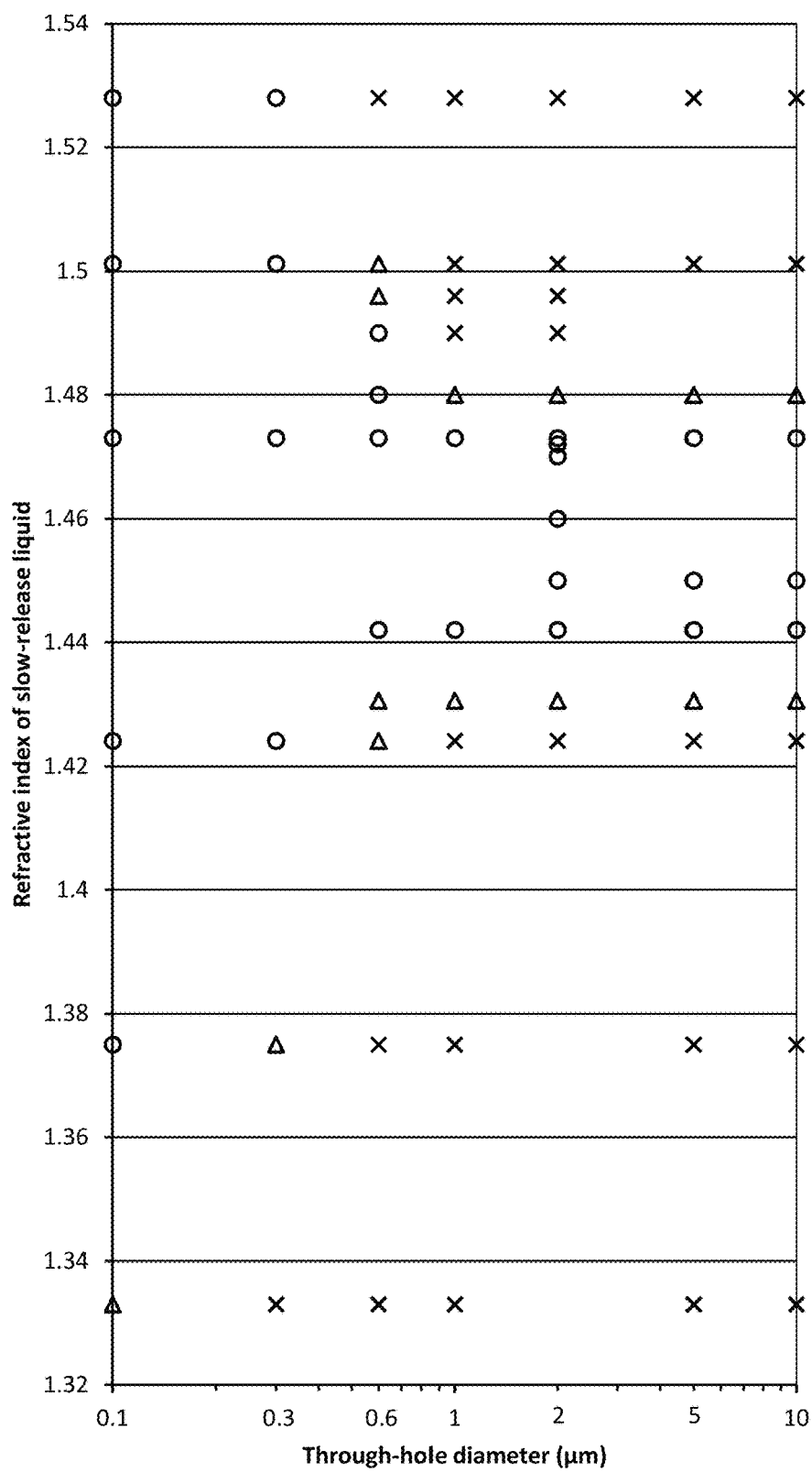
FIG. 6 is a scatter diagram showing the results of evaluation of transparency in FIG. 5.

With respect to 15 types of liquids used as sustained-release liquids in total including 6 types of aromatic oils (essential oils), 8 types of organic solvents, and water, and 7 kinds of through-hole diameters of 0.1 μm, 0.3 μm, 0.6 μm, 1 μm, 2 μm, 5 μm, and 10 μm, transparency was visually examined when the above-mentioned sustained-release liquid was absorbed into a silica monolith having a shape and size which are the same as those of a silica monolith as shown in FIG. 4, and the results obtained by visual examinations are collectively shown in a list table of FIG. 5 and a scatter diagram of FIG. 6.

Then, the above-described 7 kinds of silica monoliths having different through-hole diameters were prepared by using the above-described preparation method. Specifically, the preparation method used includes dissolving 0.6 to 1.1 g of polyethylene glycol (a molecular weight 10000), which is a coexisting substance, into 10 mL (milliliter) of a 0.01 mol/L aqueous solution of acetic acid, adding 5 mL of tetramethoxysilane (TMOS, a silica precursor), stirring the resultant to produce a homogeneous solution, which was then gelled at 40° C. to produce a gel, and immersing the gel in 0.1 M aqueous ammonia, and heating the immersed gel in a closed container at 80° C. for 24 hours, and sintering the resultant at 600° C. for 5 hours. The through-hole diameter was controlled by increasing or decreasing the amount of polyethylene glycol added. Each of the silica monoliths has the same pore diameter of 12 nm. With respect to porosity of each of the silica monoliths, a porosity was 85% for through-hole diameters of 10 μm and 2 μm, 87% for 5 μm and 1 μm, 88% for 0.6 μm, 89% for 0.3 μm, and 90% for 0.1 μm. Then, a porosity was obtained by calculating a bulk density from weight and volume of a silica monolith, and converting a value obtained by dividing the bulk density by true density of the silica monolith of 2.2 g/mL into a percentage.

In FIG. 5, results of evaluating transparency are shown as follows: "transparent", "semitransparent", and "opaque" are respectively represented by symbols of "Circle", "Triangle", and "Cross" in this order. In combinations of the above-described 15 types of sustained-release liquids and the above-described 7 kinds of through-hole diameter, combinations on which transparency were not evaluated are represented by blank. FIG. 6 is a view in which results as shown in FIG. 5 are plotted using symbols of "Circle", "Triangle", and "Cross", just as in FIG. 5, on a scatter diagram in which the abscissa is a logarithmic scale of through-hole diameter, and the ordinate is a linear scale of refractive index.

According to the results shown in FIG. 5 and FIG. 6, when a sustained-release liquid is glycerin having a refractive index of 1.473, the results are transparent independently of through-hole diameters of the silica monoliths. Thus, it is understood that a refractive index of a skeleton body of a silica monolith is the same as a refractive index of 1.473 of glycerin within the above-described second error range.

Then, with respect to the through-hole diameter of 2 µm, when refractive indexes of the sustained-release liquids are 1.442 or more and 1.473 and less, the results are transparent, when refractive indexes of the sustained-release liquids are 1.4305 and 1.48, the results are semitransparent, and when refractive indexes of the sustained-release liquids are 1.424 or less and 1.49 or more, the results are opaque. From these results, it is assumed that refractive index of the skeleton body 2 is between 1.424 and 1.49, and between 1.4305 and 1.48, and between 1.442 and 1.473. Then, when refractive index of the skeleton body 2 is defined as N, and when an upper limit of the above-described first error range is defined as D1, and when an upper limit of the above-described second error range is defined as D2, the following inequalities of Mathematical Formula 1 to Mathematical Formula 6 are obtained from refractive indexes around the above-described boundaries of refractive indexes in which the results are transparent, semitransparent, or opaque.

$$1.49 - N > D1 \quad \text{(Mathematical Formula 1)}$$

$$N - 1.424 > D1 \quad \text{(Mathematical Formula 2)}$$

$$1.48 - N \leq D1 \quad \text{(Mathematical Formula 3)}$$

$$N - 1.4305 \leq D1 \quad \text{(Mathematical Formula 4)}$$

$$1.473 - N \leq D2 < D1 \quad \text{(Mathematical Formula 5)}$$

$$N - 1.442 \leq D2 < D1 \quad \text{(Mathematical Formula 6)}$$

Further, when D1 is eliminated from the above-described Mathematical Formula 1 and Mathematical Formula 4, and when D1 is eliminated from the above-described Mathematical Formula 2 and Mathematical Formula 3, an inequality represented by the following Mathematical Formula 7 is obtained. Further, when N is eliminated from the above-described Mathematical Formula 1 and Mathematical Formula 2, and when N is eliminated from the above-described Mathematical Formula 3 and Mathematical Formula 4, an inequality represented by the following Mathematical Formula 8 is obtained. Further, when N is eliminated from the above-described Mathematical Formula 1 and Mathematical Formula 2, and when N is eliminated from the above-described Mathematical Formula 5 and Mathematical Formula 6, an inequality represented by the following Mathematical Formula 9 is obtained.

$$1.452 < N < 1.46025 \quad \text{(Mathematical Formula 7)}$$

$$0.02475 \leq D1 < 0.033 \quad \text{(Mathematical Formula 8)}$$

$$0.0155 \leq D2 < D1 < 0.033 \quad \text{(Mathematical Formula 9)}$$

From Mathematical Formula 7 to Mathematical Formula 9, it is understood that a refractive index N of a skeleton body 2 of a silica monolith according to the present embodiment falls within a range of between 1.452 and 1.46025, an upper limit D1 of a first error range falls within a range of between 0.02475 and 0.033, and an upper limit D2 of a second error range falls within a range between 0.0155 and 0.033.

From FIG. 5 and FIG. 6, when a through-hole diameter decreases within a range of 0.1 µm to 0.6 µm, a range of refractive indexes within which a result of decision is transparent is enlarged in upper and lower boundaries from a range of refractive indexes (1.442 to 1.473) when a through-hole diameter is 2 µm. Specifically, each of the ranges of refractive indexes is enlarged as follows: when a through-hole diameter is 0.6 µm, a range of refractive indexes is 1.442 to 1.49, when a through-hole diameter is 0.3 µm, a range of refractive indexes is 1.424 to 1.528, and when a through-hole diameter is 0.1 µm, a range of refractive indexes is 1.375 to 1.528. Similarly, it is understood that a range of refractive indexes within which a result of decision is transparent or semitransparent is enlarged in upper and lower boundaries from a range of refractive indexes (1.4305 to 1.48) when a through-hole diameter is 2 µm. Specifically, each of the ranges of refractive indexes is enlarged as follows: when a through-hole diameter is 0.6 µm, a range of refractive indexes is 1.424 to 1.5012, when a through-hole diameter is 0.3 µm, a range of refractive indexes is 1.375 to more than 1.528, and when a through-hole diameter is 0.1 µm, a range of refractive indexes is 1.333 to more than 1.528. That is, it is understood that when the through-hole diameter decreases in the order of 0.6 µm, 0.3 µm, and 0.1 µm, an upper limit D1 of a first error range and an upper limit D2 of a second error range increase.

On the other hand, when a through-hole diameter is larger than 0.6 µm, in order that a silica monolith can be transparent or semitransparent, it is necessary that a refractive index of a sustained-release liquid is limited to within a first error range, which is defined by an upper limit D1 of a first error range as shown in Mathematical Formula 8, with respect to a refractive index of a skeleton body 2, and in order that a silica monolith can be transparent, it is necessary that a refractive index of a sustained-release liquid is limited to within a second error range, which is defined by an upper limit D2 of a second error range as shown in Mathematical Formula 9, with respect to a refractive index of a skeleton body 2. This is apparent because, from FIG. 5 and FIG. 6, when a through-hole diameter is 1.0 µm or more, there is no difference in refractive indexes of sustained-release liquids that make silica monoliths transparent, semitransparent, or opaque.

However, when a through-hole diameter is 0.6 µm or less, each of a first error range and a second error range is enlarged, and thus each of a range of refractive index of a sustained-release liquid that can make a silica monolith transparent or semitransparent, and a range of refractive index of a sustained-release liquid that can make a silica monolith transparent is enlarged, and thus freedom in selection of a sustained-release liquid is greatly enlarged. An effect of the enlargement of freedom in selection of a sustained-release liquid is more significant when a through-hole diameter is 0.3 µm or less. For example, when ylang-ylang (an essential oil) is used as a sustained-release liquid, when a through-hole diameter is 1 µm or more, a silica monolith is still opaque, when a through-hole diameter is 0.6 µm, a silica monolith is semitransparent, and when through-hole diameter is 0.3 µm or less, a silica monolith is transparent.

Although a reason that a portion in which a sustained-release liquid is absorbed into air gaps changes to transparent or semitransparent has been described above, a conceivable reason for enlargement of a range of a refractive index within which the portion changes to transparent or semi-transparent when a through-hole diameter decreases within a range of 0.6 μm or less is as follows.

A monolithic type porous body such as a silica monolith has a periodic structure including a skeleton body and a through-hole. Further, a cycle of the periodic structure is about 2 times as large as a through-hole diameter because the through-hole diameter and a diameter of the skeleton body are substantially the same. However, since the through-hole diameter has a pore diameter distribution as shown in FIG. 2 as measured by a mercury press-in method, the cycle also has a distribution. Accordingly, it is thought that, when the cycle is about the same as a wavelength range (0.38 μm to 0.78 μm) of visible light, a geometrical optics approximation is not valid, but a wave optical phenomenon or a quantum optical phenomenon becomes manifest. Consequently, it is assumed that an influence of a difference between a refractive index of a skeleton body and a refractive index of a sustained-release liquid in air gaps is different from an influence of a difference in refractive index under a geometrical optics approximation, which results in reduction of a difference in refractive index in appearance.

A transparent porous sustained-release body is produced by providing a sustained-release liquid such as an aromatic oil having a refractive index which is the same as a refractive index of a skeleton body 2 within the above-described first or second error range which depends on a through-hole diameter, and making the sustained-release liquid to be absorbed into air gaps of a silica monolith prepared by the above-described synthesis method, and changing a portion in which the sustained-release liquid is absorbed into air gaps from an opaque state, which is an initial state, to a transparent or semitransparent state.

In a sustained-release method using a transparent porous sustained-release body, when an exposed surface of a silica monolith of the produced transparent porous sustained-release body is uncovered, a sustained-release liquid is gradually evaporated from the uncovered portion to be released to the outside of the silica monolith. Since the air of the outside intrudes into the air gaps of the portion of the silica monolith from which the sustained-release liquid is evaporated in exchange for the sustained-release liquid, the silica monolith partially becomes cloudy and thus recovers an opaque state. Accordingly, in the transparent porous sustained-release body, when the sustained-release liquid progressively released, the transparent or semitransparent portion gradually becomes cloudy and changes to an opaque state, and finally, whole of the transparent porous sustained-release body recovers an opaque state, which is the same as the initial state. That is, since a ratio between a transparent or semitransparent portion and an opaque portion of a transparent porous sustained-release body can be examined visually from the outside, a state of residual sustained-release liquid can be easily examined. Further, since a transparent state of a silica monolith changes depending on a state of residual sustained-release liquid, in addition to the above-described examination of the state of the residual sustained-release liquid, it is possible to enjoy a visual effect or an optical effect owing to changing of a transparent state, and it is further possible to add a function by application of the effect in addition to a function such as an aroma by a sustained-release liquid, release of a sustained-release liquid can be enjoyed together with the added value.

Figure 7:
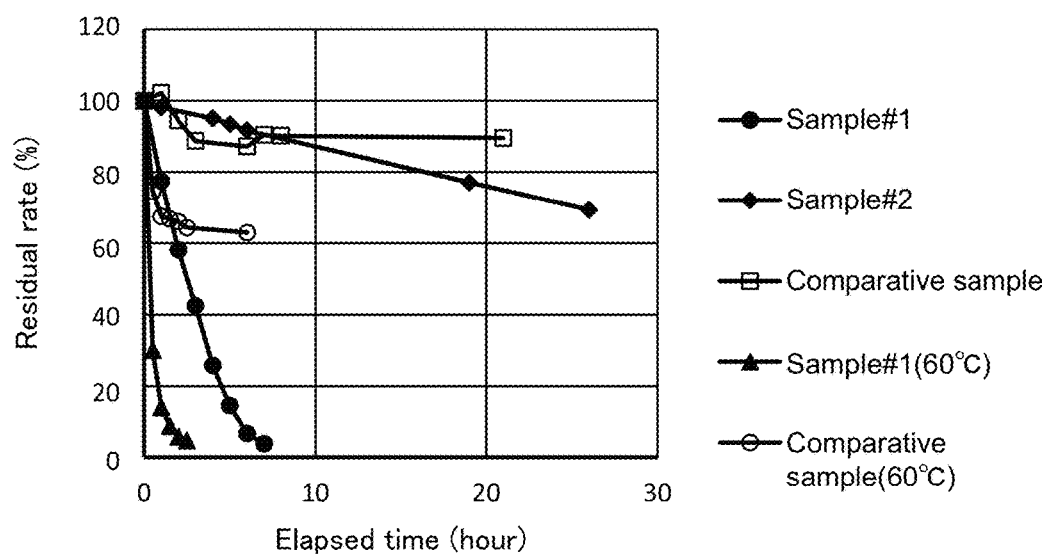
FIG. 7 is a view showing results of measurement of evaporation rate with respect to silica monoliths according to the first embodiment and a granular silica gel.

Then, a result of investigation of an evaporation rate and a method for controlling the evaporation rate of a silica monolith will be described. In FIG. 7, with respect to 3 types of samples including sample No. 1 of a cylindrical silica monolith, sample No. 2 in which a lateral face of a round column in an exposed surface of the silica monolith is covered with a glass tube and faces of upper and lower ends are uncovered, and a comparison sample of a granular silica gel as Comparative Example, results of measurement of a rate of a residual aromatic oil (%) at different elapsed time immediately after absorption of the aromatic oil into each of the samples in the following manner. The silica monoliths of sample No. 1 and No. 2 have a diameter of 4 mm, a length of 30 mm, a through-hole diameter 2 μm, a pore diameter of 12 nm, and a porosity of 85%, a glass tube of sample No. 2 has an outer diameter of 6 mm, an inner diameter of 4 mm, and a length of 30 mm, and a comparison sample has a particle diameter of 0.6 mm, a pore diameter of 2 nm, and a porosity of 20%.

A lemon essential oil having refractive index of 1.472 was used as an aromatic oil. With respect to samples No. 1 and No. 2, the lemon essential oil was dropped on an uncovered exposed surface of a silica monolith so that the lemon essential oil was absorbed until whole of the silica monolith becomes transparent. With respect to the comparison sample, a granular silica gel was placed in a test tube and dried, the lemon essential oil was put in the test tube to be infiltrated into the granular silica gel, and then the silica gel into which the lemon essential oil was completely infiltrated was removed to a watch glass. An amount of the lemon essential oil absorbed at a residual rate of 100% was calculated from a weight change between before absorption and immediately after absorption of the lemon essential oil with regard to each of the samples, an amount of the lemon essential oil absorbed at each time of measurement was calculated from a weight difference between at each time of measurement of the lemon essential oil and before absorption of the lemon essential oil with regard to each of the samples, and then the amount of the lemon essential oil absorbed at each time of measurement was divided by the above-described amount of the lemon essential oil absorbed at a residual rate of 100% to convert into a percentage, and thus a residual rate of the lemon essential oil was obtained.

With respect to sample No. 1 and a comparison sample, a lemon essential oil was emanated at two kinds of temperatures which are normal temperature and 60° C. With respect to sample No. 2, a lemon essential oil is emanated at only normal temperature.

From the results of measurement of sample No. 1 and a comparison sample shown in FIG. 7, it is understood that although an aromatic oil absorbed into a silica monolith was emanated to arrive at about a residual rate of about 2.5% or less independently of temperature conditions, an aromatic oil absorbed into a granular silica gel can be emanated to arrive at only a residual rate of 90% at normal temperature and can be emanated to arrive at a residual rate of 63% even when heated to 60° C., and thus a half or more of an aromatic oil absorbed cannot be emanated. Thus, it is understood that a silica monolith is preferable as a carrier of a sustained-release body, and the silica monolith is reusable after almost all aromatic oils are evaporated. On the other hand, it is understood that a granular silica gel is unsuitable as a carrier of a sustained-release body, and when used as a carrier of a sustained-release body, the granular silica gel is not reusable. Then, in measurement of sample No. 1, the measurement was not continued until a residual rate reaches 0% because an evaporation rate was reduced when a residual rate approaches to 0%, and thus elapsed time can be extremely extended to reduce the residual rate to around 0%, and thus the measurement was not continued.

Then, from the results of measurement of samples No. 1 and No. 2 shown in FIG. 7 at normal temperature, it is understood that an evaporation rate of an aromatic oil can be controlled by covering a part of an exposed surface of a silica monolith. Although elapsed times required to evaporate an aromatic oil until residual rates reached about 70% and about 25% were about 1.4 hours and about 4 hours respectively in sample No. 1 in which an exposed surface of a silica monolith was not covered, the elapsed times were about 26 hours and about 90 hours (data not shown in FIG. 7) in sample No. 2 in which the lateral face of a round column of a silica monolith was covered with a glass tube. In sample No. 2, elapsed times required to evaporate an aromatic oil until residual rates reached about 70% and about 25% were about 18.6 times and about 22.5 times respectively as much as those required in sample No. 1. On the other hand, an area of an uncovered exposed surface of sample No. 2 was one-sixteenth the area of an exposed surface of sample No. 1. Thus, when an uncovered area of a silica monolith is reduced to one-M th by covering an exposed surface, duration in time of emanation of aromatic oil can continue for more than M times. Then, by reducing an area of an exposed surface per a volume of a silica monolith, duration in time of emanation of aromatic oil can be extended. For example, when a diameter of sample No. 1 is doubled and a length is reduced to one-fourth, since an area of an exposed surface is reduced to about 48% with the same volume, duration in time of emanation of aromatic oil can be extended 2 or more times.

Second Embodiment

In the above-described first embodiment, an inorganic monolithic porous body 1 is assumed to have a two-step hierarchical porous structure including through-holes 3 and pores 4. However, in a second embodiment, an inorganic monolithic porous body 1 used has a one-step porous structure including a skeleton body 2 and through-holes 3 formed in voids in the skeleton body 2.

In the second embodiment, the inorganic compound that forms the skeleton body 2 is also assumed to be silica gel or silica glass ($SiO_2$). A most frequent pore diameter $\phi 1$ m in a pore diameter distribution of through-holes 3 is within a range of 2 nm or more and 100 μm, which is the same as a range including both of the most frequent pore diameter $\phi 1$ m of through-holes 3 and the most frequent pore diameter $\phi 0$ m of pores 4 of a two-step hierarchical porous structure in the first embodiment. However, as described below, when the most frequent pore diameter $\phi 1$ m of through-holes 3 is limited to 0.6 μm or less, more preferably 0.3 μm or less similarly to the first embodiment, freedom in selection of a sustained-release liquid used can be extended.

A silica monolith having a one-step porous structure is synthesized, similarly to the silica monolith having a two-step hierarchical porous structure according to the first embodiment, by a spinodal decomposition sol-gel method. Since details of a method for preparing a silica monolith using a spinodal decomposition sol-gel method has been described in the first embodiment, repetition of the description will be avoided. However, in order to provide a one-step porous structure, any one of the following 3 types of treatments will be carried out.

A first treatment method includes preparing a silica monolith having a two-step hierarchical porous structure with a pore diameter as small as possible, sintering the obtained dried gel at a temperature of 1000° C. or higher, shrinking a skeleton body to about one-half during sintering to eliminate pores formed in the skeleton body. In this case, since a through-hole diameter is also shrunk to one-half, a range of the through-hole diameter is 50 μm or less.

In a second treatment method, as described in the first embodiment, since a structure and a pore diameter of through-holes can be controlled by regulating an amount of water or a silica precursor added in a precursor sol in a sol preparation step, or by regulating a composition and an amount added of a coexisting substance, pores are eliminated in appearance by, for example, regulating an amount of polyethylene glycol, which is a coexisting substance, to control a through-hole diameter to 0.1 μm or less and thus making pore diameter distributions of through-holes and pores to be within the same range, and thus making the through-holes and the pores to be indistinguishable. In this case, although a skeleton body is a kind of a three-dimensional continuous network structure, the skeleton body has a structure similar to particle aggregates in which a granular silica gel continuously aggregates three-dimensionally. In the second embodiment, the through-holes and the pores are collectively referred to as through-holes.

In a third treatment method, since a pore diameter can be controlled by regulating, for example, temperature and time of heating in 0.1 M aqueous ammonia, the treatment is omitted to suppress formation of pores, which causes a pore diameter to be 0 μm. However, since minute pores can be formed in a part of the surface of the skeleton body, the above-described first treatment method can be added.

As one specific example of a method for preparing a silica monolith utilizing the second treatment method, a silica monolith having a one-step porous structure with a through-hole diameter of 0.1 μm or less is prepared by dissolving 1.2 g of polyethylene glycol (a molecular weight 10000), which is a coexisting substance, into 10 mL (milliliter) of 0.01 mol/L an aqueous solution of acetic acid, adding 5 mL of tetramethoxysilane (TMOS, a silica precursor), stirring to give a homogeneous solution, and then carrying out gelation at 40° C., and then immersing the gel in 0.1 M aqueous ammonia and heating at 80° C. for 24 hours in a closed container, and then sintering at 600° C. for 5 hours.

As one specific example of a method for preparing a silica monolith utilizing the third treatment method, a silica monolith having a one-step porous structure with a through-hole diameter of 1 μm is prepared by dissolving 0.9 g of polyethylene glycol (a molecular weight 10000), which is a coexisting substance, into 10 mL (milliliter) of 0.01 mol/L an aqueous solution of acetic acid, adding 5 mL of tetramethoxysilane (TMOS, a silica precursor), stirring to give a homogeneous solution, and then carrying out gelation at 40° C., and then drying the gel, and then sintering at 600° C. for 5 hours.

The third treatment method can be added to the second treatment method. As one specific example of this case, a silica monolith having a one-step porous structure with a through-hole diameter of 0.1 μm or less is prepared by dissolving 1.2 g of polyethylene glycol (a molecular weight 10000), which is a coexisting substance, into 10 mL (milliliter) of 0.01 mol/L an aqueous solution of acetic acid, adding 5 mL of tetramethoxysilane (TMOS, a silica precursor), stirring to give a homogeneous solution, and then carrying out gelation at 40° C., and then drying the gel, and then sintering at 600° C. for 5 hours.

Figure 8:
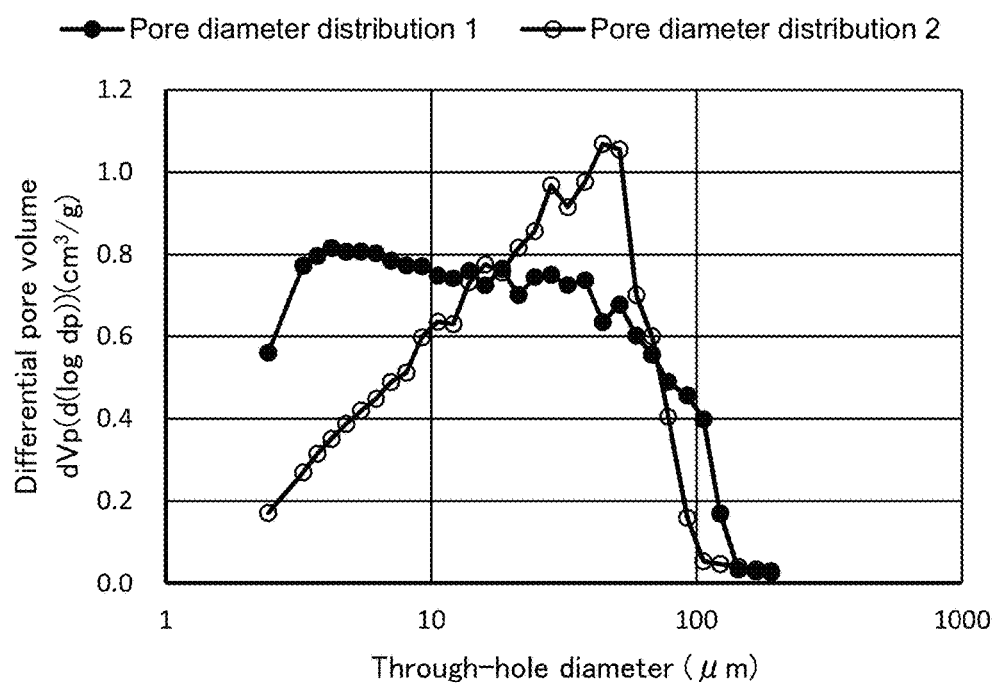
FIG. 8 is a view showing an example of pore diameter distributions of through-holes of silica monoliths according to the second embodiment.

In FIG. 8, with respect to a silica monolith prepared by the above-described second treatment method, two examples of pore diameter distributions of through-holes (pore diameter distributions 1 and 2) measured by a nitrogen adsorption desorption method. The abscissa represents a pore diameter (unit: μm) of through-holes 3, and the ordinate represents a differential pore volume (unit: cm³/g). A porosity is 77% in the pore diameter distribution 1 (a most frequent pore diameter is about 4 nm), and a porosity is 79% in the pore diameter distribution 2 (a most frequent pore diameter is about 40 nm). It is apparent from FIG. 8 that pore diameter distributions of the through-holes and the pores cannot be distinguishable from each other.

In a second embodiment, a sustained-release liquid to be absorbed into air gaps of a silica monolith is also not limited to a specific liquid as long as a state of the silica monolith is changed from an opaque state to a transparent or semitransparent state after the sustained-release liquid is absorbed into the silica monolith. That is, any liquid can be accepted as long as a refractive index of a sustained-release liquid and a refractive index of the skeleton body 2 are the same within an error range within which a portion in which the sustained-release liquid is absorbed into air gaps becomes transparent or semitransparent. However, a silica monolith is preferably transparent rather than semitransparent after absorption of a sustained-release liquid because a visual effect and an optical effect are more remarkable, and thus a sustained-release liquid is preferably a liquid with which a silica monolith is changed to a transparent state. With respect to a refractive index of a sustained-release liquid, since the description provided in the first embodiment basically applies to the second embodiment as it is, repetition of the description will be avoided.

Then, by using a combination of silica monoliths with different through-hole diameters having a one-step porous structure and various sustained-release liquids having different refractive indexes, a result of investigating an allowable range of a difference in refractive index between a refractive index of a skeleton body in which a portion in which a sustained-release liquid is absorbed into air gaps becomes transparent or semitransparent and a refractive index of the sustained-release liquid (the above-described error range) will be described.

Figure 10:
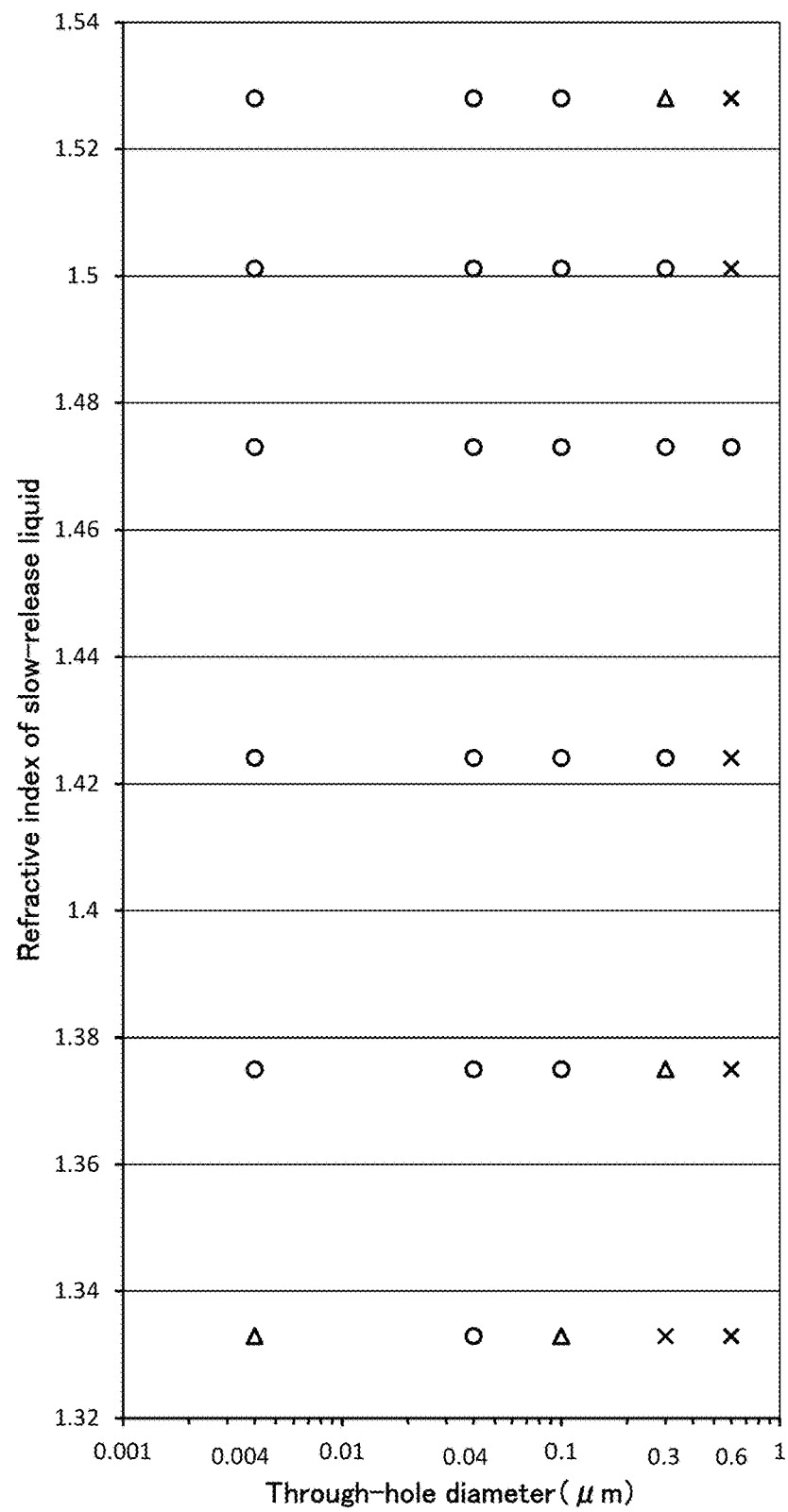
FIG. 10 is a scatter diagram showing the results of evaluation of transparency in FIG. 9.

With respect to 6 types of liquids used as sustained-release liquids in total including 5 types of organic solvents and water, and with respect to 5 kinds of through-hole diameters (a most frequent value) of 4 nm, 40 nm, 0.1 μm, 0.3 μm, 0.6 μm, transparency was visually examined when the above-mentioned sustained-release liquid was absorbed into a silica monolith at an initial state having a shape and size which are the same as those of a silica monolith as shown in FIG. 4, and the results obtained by visual examinations are collectively shown in a list table of FIG. 9 and a scatter diagram of FIG. 10.

The samples having through-hole diameters (a most frequent value) of 4 nm and 40 nm are respectively samples, which are prepared by the above-described second treatment method, having a pore diameter distribution 1 and a pore diameter distribution 2 as shown in FIG. 8. Each of the samples having through-hole diameters (a most frequent value) of 0.1 μm, 0.3 μm, and 0.6 μm are samples prepared by the above-described third treatment method.

In FIG. 9, results of evaluating transparency are shown as follows: "transparent", "semitransparent", and "opaque" are respectively represented by symbols of "Circle", "Triangle", and "Cross" in this order. In combinations of the above-described 6 types of sustained-release liquids and the above-described 5 kinds of through-hole diameter, combinations on which transparency were not evaluated are represented by blank. FIG. 10 is a view in which results as shown in FIG. 9 are plotted using symbols of "Circle", "Triangle", and "Cross", just as in FIG. 9, on a scatter diagram in which the abscissa is a logarithmic scale of through-hole diameter, and the ordinate is a linear scale of refractive index.

According to the results shown in FIG. 9 and FIG. 10, when a sustained-release liquid is glycerin having a refractive index of 1.473, the results are transparent independently of through-hole diameters of the silica monoliths. Thus, it is understood that a refractive index of a skeleton body of a silica monolith is the same as a refractive index of 1.473 of glycerin within the above-described second error range. Then, a refractive index of the skeleton body of the silica monolith falls within a range of between 1.452 and 1.46025 similarly to the first embodiment (see Mathematical Formula 7).

From FIG. 9 and FIG. 10, when a through-hole diameter decreases within a range of 0.6 μm or less, a range of refractive indexes within which a result of decision is transparent is enlarged in upper and lower boundaries from a range of refractive indexes when a through-hole diameter is 0.6 μm. Specifically, when a through-hole diameter is 0.6 μm, a result using glycerin having a refractive index of 1.473 is only transparent, and the others are opaque, however, each of the ranges of refractive indexes is enlarged as follows: when a through-hole diameter is 0.3 μm, a range of refractive indexes is 1.424 to 1.5012, and when a through-hole diameter is 0.1 μm, a range of refractive indexes is 1.375 to 1.528. Similarly, it is understood that a range of refractive indexes within which a result of decision is transparent or semitransparent is enlarged in upper and lower boundaries relative to when a through-hole diameter is 0.6 μm. Specifically, each of the ranges of refractive indexes is enlarged as follows: when a through-hole diameter is 0.3 μm, a range of refractive indexes is 1.375 to 1.528, and when a through-hole diameter is 0.1 μm, a range of refractive indexes is 1.333 to more than 1.528. That is, it is understood that when the through-hole diameter decreases in the order of 0.3 μm and 0.1 μm, an upper limit D1 of a first error range and an upper limit D2 of a second error range increase. Further, when a through-hole diameter is 40 nm, a silica monolith becomes transparent even using water having a refractive index of 1.333. On the contrary, when a through-hole diameter is 4 nm, a silica monolith becomes semitransparent using water similarly to when a through-hole diameter is 0.1 μm. When through-hole diameters are 4 nm and 40 nm, since width and shape of pore diameter distributions vary, it is difficult to compare them simply on the basis of a difference of through-hole diameters. However, when a through-hole diameter is 0.1 μm or less, as compared to when a through-hole diameter is 0.3 μm, a range of refractive index within which a result of decision is transparent and a range within which a result of decision is transparent or semitransparent are obviously enlarged. That is, it is understood that when the through-hole diameter decreases in the order of 0.3 μm, 0.1 μm, and 40 nm, an upper limit D1 of a first error range and an upper limit D2 of a second error range increase.

Next, the results of measurement in FIG. 9 and FIG. 10 and the results of measurement in FIG. 5 and FIG. 6 of the first embodiment are compared. In the case of a through-hole diameter of 0.6 μm, when dichloromethane having a refractive index of 1.424 and benzene having a refractive index of 1.5012 are absorbed, the silica monoliths of the first embodiment having a two-step hierarchical porous structure become semitransparent, however, each of the silica monoliths of the second embodiment having a one-step porous structure is opaque. Further, in the case of a through-hole diameter of 0.3 μm, when benzonitrile having a refractive index of 1.528 is absorbed, a silica monolith of the first embodiment having a two-step hierarchical porous structure is transparent, however, a silica monolith of the second embodiment having a one-step porous structure becomes semitransparent. Thus, it is understood that, in the case of through-hole diameters of 0.6 μm and 0.3 μm, when a silica monolith having a two-step hierarchical porous structure is replaced with a silica monolith having a one-step porous structure, the first error range and the second error range tend to be slightly reduced. However, it is understood that, in a silica monolith having a one-step porous structure, since a through-hole diameter can further be reduced to less than 0.1 μm, the first error range and the second error range are susceptible to slight enlargement.

The reason that, when through-hole diameters are 0.6 μm and 0.3 μm, the first error range and the second error range slightly vary with presence or absence of pores is thought to be basically the same as that described in the first embodiment as a reason that a range of a refractive index within which a result of decision is transparent or semitransparent is enlarged when a through-hole diameter decreases within a range of 0.6 μm or less. That is, it is thought that since pores having a pore diameter of smaller than a wavelength range of visible light (0.38 μm to 0.78 μm) are dispersively formed on a surface of a skeleton body, a difference between a refractive index of a skeleton body and a refractive index of a sustained-release liquid in air gaps is further reduced in appearance. Consequently, it is assumed that when the pores do not exist, the effect of the reduction is reduced, and thus the first error range and the second error range become slightly narrow.

Since a method for producing a transparent porous sustained-release body, a sustained-release method using a transparent porous sustained-release body, an evaporation rate with respect to a silica monolith, and a method for controlling the evaporation rate are basically the same as those described in the first embodiment, repetition of the descriptions will be avoided.

Third Embodiment

In the above-described first and second embodiments, although the description was provided on the assumption that a user uses a completed transparent porous sustained-release body, it is also possible to provide a kit of sustained-release body to a user, which includes separately an initial state inorganic monolithic porous body (a silica monolith) and the above-described sustained-release liquid constituting a transparent porous sustained-release body. In this case, a user can complete a transparent porous sustained-release body described in the above-described first and second embodiments by dropping the sustained-release liquid on an exposed surface of the initial state inorganic monolithic porous body to be absorbed into air gaps so as to change a state of the inorganic monolithic porous body from an opaque state to a transparent or semitransparent state.

Then, a sustained-release liquid contained in the kit of sustained-release body is not limited to one type, and two or more types of sustained-release liquids can be attached. In this case, when one type of sustained-release liquid is evaporated to arrive at a residual rate of 0% or around 0%, then a user can complete another new transparent porous sustained-release body by making another type of sustained-release liquid to be absorbed into air gaps of the same inorganic monolithic porous body. When the two or more types of sustained-release liquid are different types of aromatic oils, a user can enjoy two or more different types of flavors. In this case, when the through-hole diameter of the inorganic monolithic porous body is 0.3 μm or less, as described in the first embodiment, it is preferred because freedom in selection of an aromatic oil used is extended.

Other Embodiments

A modified example of the above-described first to third embodiments is described below.

<1> A transparent porous sustained-release body of the above-described first or second embodiment, or an inorganic monolithic porous body of a kit of sustained-release body of the above-described third embodiment is not limited to an unglazed body, and can be provided in a form in which a part of an exposed surface of an inorganic monolithic porous body is covered with, for example, a transparent glass tube as described in the first embodiment. The cover material can be unremovably fixed to an inorganic monolithic porous body, or can be fixed in freely attachable and detachable manner, or the cover material can have a form in which a user affixes the cover material.

Further, two or more cover materials which differ in at least one of, for example, shape, color, and material can be included in a transparent porous sustained-release body or a kit of sustained-release body as appurtenances.

Figure 11:
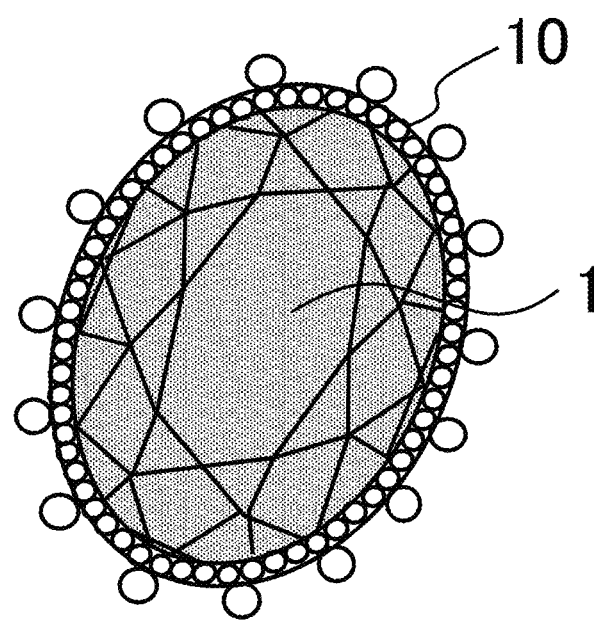

In order to impart a factor of design to an inorganic monolithic porous body, for example, as shown in FIG. 11, it is a preferred embodiment that a base 10 such as a finger ring or a brooch is used, and an inorganic monolithic porous body 1 formed in a shape which can be suitably placed on a base 10 is affixed, as the above-described cover material, to a portion for carrying a jewel or the like. As one example for enjoying the above-described visual effect of a sustained-release method, when a character, a figure, or the like is provided at a portion on which an inorganic monolithic porous body 1 is affixed, and when a sustained-release liquid is absorbed to change an inorganic monolithic porous body 1 to a transparent state, a visual effect that the character, figure, or the like is visible through the inorganic monolithic porous body 1 can be enjoyed.

Figure 12:
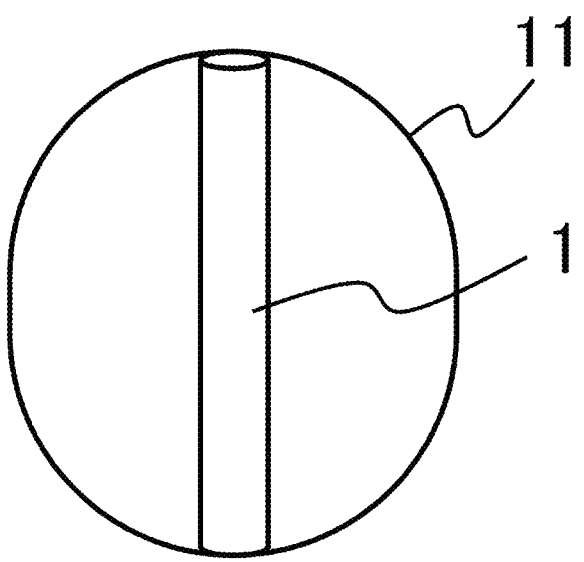
FIG. 12 is a view schematically showing one example in which a part of an exposed surface of an inorganic monolithic porous body is covered with glass.

Further, as another embodiment, for example, as exemplified in FIG. 12, melted glass can be adhered to a lateral face of a column-shaped inorganic monolithic porous body 1 to provide any shape such as spherical shape, and then cooled to give a cover material 11 made of glass. Further, it is possible, using melted glass as an adhesive and also as the above-described cover material, to combine two or more inorganic monolith porous bodies 1 and form the combined inorganic monolithic porous bodies 1 into any shape.

<2> Although a surface of a skeleton body of an inorganic monolithic porous body of each of the above-described embodiments does not have a surface modification, an inorganic monolithic porous body having a surface modification can be used with the proviso that when the surface of the skeleton body has some surface modification, the above-described first and second error range are not affected and a transparent state after absorption of a sustained-release liquid does not vary from that of an inorganic monolithic porous body having no surface modification, or that if the above-described first and second error range are affected, an inorganic monolithic porous body changes to a transparent state after absorption of a sustained-release liquid similarly to an inorganic monolithic porous body having no surface modification.

Two types of samples (an octadecylated silica monolith and a phenylated silica monolith), respectively, having different one of two types of functional groups (an octadecyl group and a phenyl group) on a silica monolith having a through-hole diameter of 2 μm and a pore diameter of 12 nm used in evaluation results of transparency shown in FIG. 5 and FIG. 6 according to the first embodiment were provided, and transparency was evaluated using 5 types of aromatic oil, which are the same as 6 types of aromatic oils (essential oils) used in a transparency evaluation of FIG. 5 and FIG. 6 without coconut oil. The results of the evaluation were identical with that of a silica monolith having no a surface modification.

Then, an octadecylated silica monolith can be prepared by, as an example, drying a silica monolith at 150° C., and then immersing the dried silica monolith in a toluene solution containing 10% of octadecyltrimethoxysilane, heating to reflux for 12 hours, immersing the obtained silica monolith in ethanol to substitute the solvent, and drying the silica monolith. A phenylated silica monolith can be prepared by using phenyltrimethoxysilane instead of octadecyltrimethoxysilane.

A method for introducing a functional group generally includes a method in which a functional group is chemically fixed to a surface of a skeleton body via a covalent bond, or a method in which a functional group is physically fixed to a surface of a skeleton body by physical interaction such as ionic bonding or hydrophobic interaction. For example, a method for chemically introducing a functional group includes a method in which a functional group is fixed via a hydroxyl group on a surface of a skeleton body ($SiO_2$) by reacting a silane coupling agent having a functional group.

A surface modification of an inorganic monolithic porous body also includes, in addition to the above-described surface modification of functional group, a surface modification in which a metallic salt of a transition metal element is attached to a surface of the skeleton body, and then the inorganic monolithic porous body is oxidized, and the inorganic monolithic porous body is colored in a color particular to the transition metal. By forming the oxide film having a thickness thinner than wavelengths of visible light, and when the above-described sustained-release liquid is absorbed into air gaps, the inorganic monolithic porous body is a transparent or semitransparent state colored in the above-described particular color. As one example for forming the oxide film, a solution of a transition metal element compounds is impregnated into an inorganic monolithic porous body, a metallic salt of a transition metal element is adsorbed into a surface of the skeleton body, the resultant is naturally dried and then sintered by using an electric furnace at 900° C., and the above-described metallic salt is oxidized, and thus coloring can be accomplished. For example, when the above-described solution is an ethanol solution of iron (II) chloride, an inorganic monolithic porous body is colored in orange, and when the above-described solution is an ethanol solution of cobalt, an inorganic monolithic porous body is colored in blue. Then, although a solution containing a cation such as cobalt is adsorbed on a surface of a skeleton body, especially, when an inorganic monolithic porous body is immersed using a dilute solution, the cation is strongly adsorbed at an around periphery of an inorganic monolithic porous body and does not infiltrate into the body, and thus an exposed surface of the inorganic monolithic porous body is principally covered, and as a result, the exposed surface of the inorganic monolithic porous body appears bluish.

<3> In a sustained-release method as described in the above-described first embodiment, it is briefly described that since a transparent state of an inorganic monolithic porous body varies depending on a state of residual sustained-release liquid, a visual effect or an optical effect owing to changing in transparent state can be enjoyed, and an application of the effects is also briefly described. As an application of the effects, an inorganic monolithic porous body in a transparent state is irradiated with an incident visible light, the incident light is passed through the inorganic monolithic porous body, and the incident light is emitted from the inorganic monolithic porous body toward the outside, and thus a part or whole of the inorganic monolithic porous body can be bright in a color of the incident light.

Figure 13A:
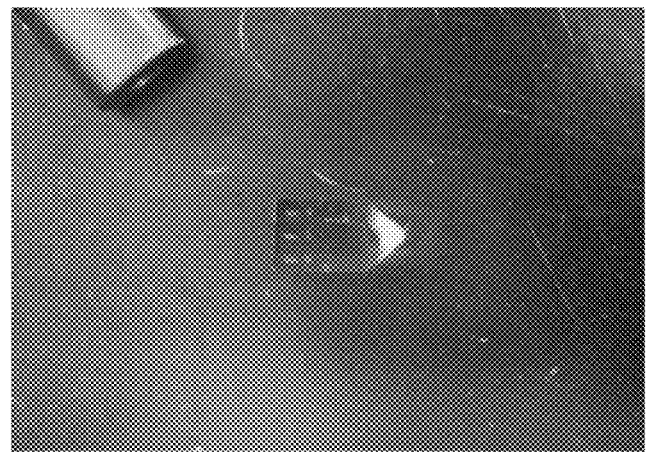
FIGS. 13(A) and (B) are photographs showing an example of visual effects when silica monoliths are irradiated with an incident laser beam.
Figure 13B:
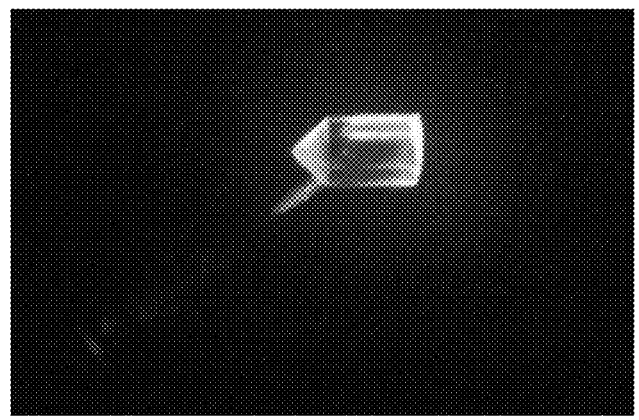

In FIG. 13, one end of a silica monolith having hexagonal column-shape is processed into conic to provide a pencil shape, and the pencil shaped silica monolith is impregnated with a sustained-release liquid to be a transparent state. Then, a photograph (A) showing a situation in which the flat end face of the pencil shaped silica monolith is irradiated with an incident red laser beam, and a photograph (B) showing a situation in which the conic end face of the same pencil shaped silica monolith is irradiated with an incident red laser beam are provided. The two photographs have been changed to monochrome images. Thus, although it is hard to be recognized, in (A), whole of the silica monolith is reddish and a tip portion of the conic shines at high-intensity, and in (B), whole of the silica monolith shines with reddish color.

In an example shown in FIG. 13, it is exemplified that a handheld laser pointer is used as a light source of an incident light which intrudes into a silica monolith, and a portion at which an incident light enters is manually adjusted by a user. However, positional relationship between a silica monolith and a light source can be fixed to constitute a sustained-release apparatus. For example, a light source such as a laser, or a light emitting diode can be affixed to a base or a flame on which a silica monolith is mounted or fixed, and a silica monolith can be affixed at a portion which has a predetermined positional relationship to the light source. As one example, it is preferred to affix the above-described light source to a portion of a base 10, as described in <1> above, such as a finger ring and a brooch on which, for example, a character or a figure is provided. Then, a positional relationship between a silica monolith and a light source can be constituted so that a user can change as required.

Further, it is also preferred that particles of a fluorescent substance are fixed on an exposed surface of an inorganic monolithic porous body or a surface of the skeleton body. However, an amount of the granules of fluorescent substance added and a particle diameter should be adjusted so that the particles of the fluorescent substance do not prevent the inorganic monolithic porous body in which a sustained-release liquid is absorbed from changing to transparent or semitransparent. Then, although a fluorescent substance which can be used includes various types of well-known fluorescent substances such as a blue fluorescent substance, a green fluorescent substance, a red fluorescent substance, an orange fluorescent substance, or a yellow fluorescent substance, the fluorescent substance used is required to be excited by a light having a wavelength of a light source used. Then, a fluorescent substance is not limited to one type, and two or more fluorescent substances having different emission wavelengths can be used. A light source used is preferably a light source of relatively short wavelength such as ultraviolet rays or a blue ray. When such an inorganic monolithic porous body containing one type, or two or more types of granules of fluorescent substance is used, the fluorescent substance is excited by an incident light of the inorganic monolithic porous body, a light having a color depending on the fluorescent substance is emitted, and then the color of the light emitted from the fluorescent substance and the color of the light from the light source are mixed to provide a mixed color to the inorganic monolithic porous body. However, when a light from a light source is ultraviolet rays, a color of a light from a light source does not produce a mixed color.

As a method for fixing particles of a fluorescent substance to a surface of the skeleton body of an inorganic monolithic porous body, the following method can be adopted. A fluorescent substance is micro pulverized into a fine powder having a size of about 0.1 to 0.5 μm using a planetary mill, and a suspension in which the fine powder of fluorescent substance is dispersed in ethanol is prepared. An inorganic monolithic porous body is immersed in the suspension of the fine powder of fluorescent substance, and then the inorganic monolithic porous body is immediately recovered and dried to attach the fine powder of fluorescent substance to a surface of the skeleton body. Then, a heat treatment is carried out at 800° C. to fix the fine powder of fluorescent substance to the surface of the skeleton body.

As a method for fixing particles of a fluorescent substance to an exposed surface of an inorganic monolithic porous body, the following method can be adopted. A fluorescent substance is ground into powder of fluorescent substance having a size of, for example, about 5 μm using a mill, the powder of fluorescent substance is dispersed in glycerin and applied to an exposed surface of an inorganic monolithic porous body, and then a heat treatment is carried out at 800° C. to fix the powder of fluorescent substance to the exposed surface of the inorganic monolithic porous body. It is preferred that a part of an exposed surface is uncovered for an incident light from a light source or injection of a sustained-release liquid compared to applying powder of fluorescent substance to the whole exposed surface of the inorganic monolithic porous body. Further, when simply carrying out a heat treatment at 800° C., fixation of powder of fluorescent substance is weak, and thus it is preferred that powder of fluorescent substance dispersed in glycerin is applied to an exposed surface of an inorganic monolithic porous body, the resultant is covered with a transparent glass tube, and then the glass tube is melted at 900° C., the powder of fluorescent substance stuck to the exposed surface of the inorganic monolithic porous body is bonded with the melted glass to fix strongly. Then, instead of covering with a transparent glass tube or the like, it is possible that melted glass is adhered to the exposed surface, and the resultant is cooled.

<4> In each of the above-described embodiments, although an aromatic liquid such as aromatic oil is assumed as an example of a sustained-release liquid, a sustained-release liquid is not limited to an aromatic liquid, and it can be a liquid containing, for example, a deodorant component or an insecticidal ingredient, or a liquid only for changing transparency of an inorganic monolithic porous body 1 from an opaque state at an initial state to transparent or semitransparent.

<5> In each of the above-described embodiments, although silica (silica gel or silica glass) is assumed as an inorganic compound to constitute a skeleton body 2 of an inorganic monolithic porous body 1, the inorganic compound is not limited to a silica, and it can be a silicon oxide composite containing mainly a silicon oxide, and further an oxide porous body containing a typical metal element such as aluminum, phosphorus, germanium, and tin, or a transition metal element such as titanium, zirconium, vanadium, chromium, iron, cobalt, nickel, palladium, platinum, copper, silver, gold, and zinc can also be used. Further, in addition to the above, an inorganic oxide porous body including a composite containing an alkali metal element such as lithium and sodium, an alkaline earth metal element such as magnesium and calcium, a lanthanide series element such as lanthanum and cerium can also be used.

However, when an inorganic compound varies, a refractive index of a skeleton body 2 is different from that of a silica monolith, and a refractive index of a sustained-release liquid which is the same as a refractive index of the skeleton body 2 within the above-described first or second error range is also different, and thus it is possible that a sustained-release liquid suitable for a purpose cannot be selected.

<6> In each of the above-described embodiments, with respect to a method for synthesizing an inorganic monolithic porous body, descriptions are provided with reference to examples which expressly show specific values (e.g., volumes, a temperature, or time), the synthesis method is not limited to the conditions of values exemplified in the examples.

INDUSTRIAL APPLICABILITY

A porous sustained-release body, a kit of sustained-release body, a sustained-release method, a sustained-release apparatus, and a method for producing a transparent porous sustained-release body according to the present invention can be used for a porous sustained-release body which can gradually emanate a predetermined liquid and change transparency of a porous carrier.

DESCRIPTION OF SYMBOLS

1 Inorganic monolithic porous body
2 Skeleton body
3 Through-holes
4 Pores
10 Base
11 Cover material made of glass

The invention claimed is:

1. A transparent porous sustained-release body comprising an inorganic monolithic porous body including a skeleton body of an inorganic compound and air gaps having a three-dimensional continuous network structure, and a sustained-release liquid absorbed into said air gaps,
  wherein
  said inorganic monolithic porous body is opaque at an initial state, which is a state before absorption of said sustained-release liquid in which air exists in said air gaps,
  a refractive index of said sustained-release liquid and a refractive index of said skeleton body are the same within an error range such that a portion in which said sustained-release liquid is absorbed into said air gaps changes to transparent or semitransparent;
  said skeleton body has a three-dimensional continuous network structure,
  said air gaps have a two-step hierarchical porous structure including through-holes and pores, the through-holes being formed in voids in said skeleton body and having a three-dimensional continuous network structure, and the pores extending from a surface to an inside of said skeleton body and being dispersively formed on said surface,
  a most frequent pore diameter in a pore diameter distribution of said pores is within a range of 2 nm or more and 200 nm or less,
  a most frequent pore diameter in a pore diameter distribution of said through-holes is equal to or more than 5 times of said most frequent pore diameter of the pores, and within a range of 0.1 μm or more and 100 μm or less, said refractive index of said skeleton body is 1.45 to 1.5, and said refractive index of said sustained-release liquid is 1.4305 to 1.48 when said most frequent pore diameter of said through-holes is more than 0.6 μm, 1.424 to 1.5012 when said most frequent pore diameter of said through-holes is more than 0.3 μm and equal to or less than 0.6 μm, and 1.375 to 1.528 when said most frequent pore diameter of said through-holes is equal to or less than 0.3 μm.

2. The transparent porous sustained-release body according to claim 1, wherein a most frequent pore diameter in a pore diameter distribution of said through-holes is 0.6 μm or less.

3. The transparent porous sustained-release body according to claim 1, wherein a most frequent pore diameter in a pore diameter distribution of said through-holes is 0.3 μm or less.

4. The transparent porous sustained-release body according to claim 1, wherein said inorganic compound is a silicon oxide composite mainly containing silica or silicon oxide.

5. The transparent porous sustained-release body according to claim 1, wherein said sustained-release liquid is an essential oil having a refractive index within a range of 1.4 to 1.6, and the refractive index of the essential oil is the same relative to the refractive index of said skeleton body within said error range.

* * * * *